(12) United States Patent
Foncelle et al.

(10) Patent No.: US 8,637,729 B2
(45) Date of Patent: Jan. 28, 2014

(54) F. OXYSPORUM F.SP. MELONIS RACE 1,2-RESISTANT MELONS

(75) Inventors: Bruno Foncelle, Sarrians (FR); Gregori Bonnet, Sarrians (FR); Marc Oliver, Saint-Sauveur (FR)

(73) Assignee: Syngenta Participations AG, Basel (CH)

( * ) Notice: Subject to any disclaimer, the term of this patent is extended or adjusted under 35 U.S.C. 154(b) by 231 days.

(21) Appl. No.: 12/451,996

(22) PCT Filed: Jun. 19, 2008

(86) PCT No.: PCT/EP2008/057770
§ 371 (c)(1), (2), (4) Date: Mar. 10, 2010

(87) PCT Pub. No.: WO2009/000736
PCT Pub. Date: Dec. 31, 2008

(65) Prior Publication Data
US 2010/0235941 A1   Sep. 16, 2010

(30) Foreign Application Priority Data
Jun. 22, 2007   (EP) .................................... 07110860

(51) Int. Cl.
*A01H 4/00* (2006.01)
*A01H 5/10* (2006.01)
*A01H 5/00* (2006.01)

(52) U.S. Cl.
USPC .......................... 800/267; 800/260; 800/266

(58) Field of Classification Search
None
See application file for complete search history.

(56) References Cited

PUBLICATIONS

Perchepied et al (2005 Theor Appl Genet 111:65-74, provided in Applicants IDS.*
L. Perchepied et al., Theor Appl Genet, 2005, 111, pp. 65-74.
L. Perchepied et al., Phytopathology, 2004, 94, 12, pp. 1331-1336.
Herman et al., Proceedings of the IX Eucarpia Meeting on Genetics and Breeding of Cucurbitaceae, 2008, pp. 149-156.
Perin et al., Theor Appl Genet, 2002, 104, pp. 1017-1034.

* cited by examiner

*Primary Examiner* — Brent T Page
(74) *Attorney, Agent, or Firm* — Karen Magri

(57) ABSTRACT

Methods for conveying *Fusarium oxysporum* f.sp. *melonis* (FOM) race 1,2 resistance into non-resistant melon germplasm are provided, in some embodiments, the methods include introgressing FOM race 1,2 resistance into a non-resistant melon using one or more nucleic acid markers for marker-assisted selection among melon lines to be used in a melon breeding program, wherein the markers are linked to FOM race 1,2 resistance. Also provided are quantitative trait loci (QTLs) associated with resistance to FOM race 1,2; isolated and purified genetic markers associated with FOM race 1,2 resistance; melon plants, seeds, and tissue cultures produced by any of the disclosed methods; fruit and seed produced by the disclosed melon plants; and compositions including amplification primer pairs capable of initiating DNA polymerization by a DNA polymerase on melon nucleic acid templates to generate melon marker amplicons.

9 Claims, No Drawings

F. OXYSPORUM F.SP. MELONIS RACE 1,2-RESISTANT MELONS

CROSS-REFERENCE TO RELATED APPLICATIONS

This application is a national phase application of International Application No. PCT/EP2008/057770, filed Jun. 19, 2008, which claims priority to European Application No. 07110860.9, filed Jun. 22, 2007.

TECHNICAL FIELD

The presently disclosed subject matter relates to melons, such as melons of the species *Cucumis melo*, and methods of breeding the same. More particularly, the presently disclosed subject matter relates to melon lines, such as *Cucumis melo* lines, with improved resistance to. *Fusarium oxysporum* f.sp. *melonis* race 1,2 infection and methods of breeding same, the methods involving genetic marker analysis.

BACKGROUND

Plant pathogens are known to cause massive damage to important crops, resulting in significant agricultural losses with widespread consequences for both the food supply and other industries that rely on plant materials. As such, there is a long felt need to reduce the incidence and/or impact of agricultural pests on crop production.

An example of such pathogens is the *Fusarium oxysporum* genus of plant fungi. *F. oxysporum* is known to devastate various crop plants including, but not limited to pea, banana, cotton, tomato, and others. *F. oxysporum* is characterized by several different specialized forms, which are referred to as formae specialis (f.sp.), each of which infect a variety of hosts to cause disease. There are at least 48 different formae speciales of *F. oxysporum*.

One particular formae special's of *F. oxysporum* is. *F. oxysporum* f.sp. melonis (FOM), which infects various melons of the species *Cucumis melo*, which includes European cantaloupes and includes muskmelons such as American cantaloupes, sugar melons, honeydews, and Casaba. Several races have been identified for FOM, and include races 0, 1, 2, and 1,2. Additionally, two genes, Fom-1 and Fom-2, have been identified that are associated with resistance to races 0 and 2, and 0 and 1, respectively (Risser et al., 1976).

What are needed, then, are new hybrid and/or inbred *Cucumis melo* varieties that are resistant to FOM race 1,2, and new methods for introducing increased resistance to FOM race 1,2 in melons.

SUMMARY

This Summary lists several embodiments of the presently disclosed subject matter, and in many cases lists variations and permutations of these embodiments. This Summary is merely exemplary of the numerous and varied embodiments. Mention of one or more representative features of a given embodiment is likewise exemplary. Such an embodiment can typically exist with or without the feature(s) mentioned; likewise, those features can be applied to other embodiments of the presently disclosed subject matter, whether listed in this Summary or not. To avoid excessive repetition, this Summary does not list or suggest all possible combinations of such features.

The presently disclosed subject matter provides methods for conveying *Fusarium oxysporum* f.sp. *melonis* (FOM) race 1,2 resistance into non-resistant melon germplasm. In some embodiments the methods comprise introgressing FOM race 1,2 resistance into a non-resistant melon using one or more nucleic acid markers for marker-assisted selection among melon lines to be used in a melon breeding program, wherein the markers are linked to FOM race 1,2 resistance. In some embodiments, the one or more nucleic acid marker is selected from the group consisting of 3.1, 3.2, 6.1, 6.2, 7.1, 7.2, 9.1, 9.2, 9.3, 10.1, and 10.2. In some embodiments, the one or more nucleic acid markers are selected from the group consisting of 3.1, 3.2, 9.1, 9.2, and 9.3. In some embodiments, the marker-assisted selection comprises the use of an analysis technique selected from the group consisting of RAPD analysis, RFLP analysis, microsatellite analysis, and AFLP analysis. In some embodiments, the methods further comprise screening an introgressed melon for orange flesh.

The presently disclosed subject matter also provides methods for reliably and predictably introgressing FOM race 1,2 resistance into non-resistant melon germplasm. In some embodiments, the methods comprise using one or more nucleic acid markers for marker-assisted selection among melon lines to be used in a melon breeding program, wherein the nucleic acid markers are selected from the group consisting of 3.1, 3.2, 6.1, 6.2, 7.1, 7.2, 9.1, 9.2, 9.3, 10.1, and 10.2, and introgressing the resistance into the non-resistant melon germplasm. In some embodiments, the one or more nucleic acid markers are selected from the group consisting of 3.1, 3.2, 9.1, 9.2, and 9.3. In some embodiments, the marker-assisted selection comprises the use of an analysis technique selected from the group consisting of RAPD analysis, RFLP analysis, microsatellite analysis, and AFLP analysis. In some embodiments, the methods further comprise screening an introgressed melon for orange flesh.

The presently disclosed subject matter also provides methods for the production of an inbred melon plant adapted for conferring, in hybrid combination with a suitable second inbred, resistance to *F. oxysporum* f.sp. melon's (FOM) race 1,2. In some embodiments, the methods comprise (a) selecting a first donor parental line possessing a desired FOM race 1,2 resistance and having at least one of the resistant loci selected from a locus mapping to linkage group 3 and mapped by one or more of the markers 3.1 and 3.2 and a locus mapping to linkage group 9 and mapped by one or more of the markers 9.1, 9.2, and 9.3; (b) crossing the first donor parent line with a second parental line in hybrid combination, to produce a segregating plant population; (c) screening the segregating plant population for identified chromosomal loci of one or more genes associated with the resistance to FOM race 1,2; and (d) selecting plants from the population having the identified chromosomal loci for further screening until a line is obtained which is homozygous for resistance to FOM race 1,2 at sufficient loci to give resistance to FOM race 1,2 in hybrid combination. In some embodiments, the methods further comprise screening the plants of the line that is homozygous for resistance to FOM race 1,2 at sufficient loci to give resistance to FOM race 1,2 in hybrid combination for the presence of orange flesh. In some embodiments, the methods further comprise screening one or more members of the segregating plant population of the selected plants for orange flesh.

The presently disclosed subject matter also provides methods for producing melon plants which are resistant to *F. oxysporum* f.sp. *melonis* (FOM) race 1,2 occurring in melon. In some embodiments, the methods comprise (a) providing a *Cucumis melo* plant which contains one or more alleles that confer resistance to FOM race 1,2, which alleles are characterized one or more of five Quantitative Trait Loci QTL1-QTL5 on different chromosomes, wherein (i) QTL1 is defined by the following markers: (1) a marker of about 322 basepairs (bp), wherein the marker corresponds to an amplification product generated by amplifying a *Cucumis melo* nucleic acid with a forward primer comprising a nucleotide sequence as set forth in SEQ ID NO: 1 and a reverse primer comprising a nucleotide sequence as set forth in SEQ ID NO: 2; and (2) a marker of about 303 bp, wherein the marker corresponds to an amplification product generated by amplifying a *Cucumis melo* nucleic acid with a forward primer comprising a nucleotide sequence as set forth in SEQ ID NO: 3 and a reverse primer comprising a nucleotide sequence as set forth in SEQ ID NO: 4, or any part of a DNA sequence as in 03MFR001795 linked within 1, 2, 5, or 10 cM to at least one of the markers of (1) and (2) conferring resistance to FOM race 1,2; (ii) QTL2 is defined by the following markers: (1) a marker of about 237 bp, wherein the marker corresponds to an amplification product generated by amplifying a *Cucumis melo* nucleic acid with a forward primer comprising a nucleotide sequence as set forth in SEQ ID NO: 5 and a reverse primer comprising a nucleotide sequence as set forth in SEQ ID NO: 6; and (2) a marker of about 189 bp, wherein the marker corresponds to an amplification product generated by amplifying a *Cucumis melo* nucleic acid with a forward primer comprising a nucleotide sequence as set forth in SEQ ID NO: 7 and a reverse primer comprising a nucleotide sequence as set forth in SEQ ID NO: 8, or any part of a DNA sequence as in 03MFR001795 linked within 1, 2, 5, or 10 cM to at least one of the markers of (1) and (2) conferring resistance to FOM race 1,2; (iii) QTL3 is defined by the following markers: (1) a marker of about 221 bp, wherein the marker corresponds to an amplification product generated by amplifying a *Cucumis melo* nucleic acid with a forward primer comprising a nucleotide sequence as set forth in SEQ ID NO: 9 and a reverse primer comprising a nucleotide sequence as set forth in SEQ ID NO: 10; and (2) a marker of about 229 bp, wherein the marker corresponds to an amplification product generated by amplifying a *Cucumis melo* nucleic acid with a forward primer comprising a nucleotide sequence as set forth in SEQ ID NO: 11 and a reverse primer comprising a nucleotide sequence as set forth in SEQ ID NO: 12, or any part of a DNA sequence as in 03MFR001795 linked within 1, 2, 5, or 10 cM to at least one of the markers of (1), and (2) conferring resistance to FOM race 1,2; (iv) QTL4 is defined by the following markers: (1) a marker of about 329 bp, wherein the marker corresponds to an amplification product generated by amplifying a *Cucumis melo* nucleic acid with a forward primer comprising a nucleotide sequence as set forth in SEQ ID NO: 13 and a reverse primer comprising a nucleotide sequence as set forth in SEQ ID NO: 14; (2) a marker of about 279 bp, wherein the marker corresponds to an amplification product generated by amplifying a *Cucumis melo* nucleic acid with a forward primer comprising a nucleotide sequence as set forth in SEQ ID NO: 15 and a reverse primer comprising a nucleotide sequence as set forth in SEQ ID NO: 16; and (3) a marker of about 147 bp, wherein the marker corresponds to an amplification product generated by amplifying a *Cucumis melo* nucleic acid with a forward primer comprising a nucleotide sequence as set forth in SEQ ID NO: 17 and a reverse primer comprising a nucleotide sequence as set forth in SEQ ID NO: 18, or any part of a DNA sequence as in 03MFR001795 linked within 1, 2, 5, or 10 cM to at least one of the markers of (1), (2), and (3) conferring resistance to FOM race 1,2; and (v) QTL5' is defined by the following markers: (1) a marker of about 246 bp, wherein the marker corresponds to an amplification, product generated by amplifying a *Cucumis melo* nucleic acid with a forward primer comprising a nucleotide sequence as set forth in SEQ ID NO: 1.9 and a reverse primer comprising a nucleotide sequence as set forth in SEQ ID NO: 20; and (2) a marker of about 251 bp, wherein the marker corresponds to an amplification product generated by amplifying a *Cucumis melo* nucleic acid with a forward primer comprising a nucleotide sequence as set forth in SEQ ID NO: 21 and a reverse primer comprising a nucleotide sequence as set forth in SEQ ID NO: 22, or any part of a DNA sequence as in 03MFR001795 linked within 1, 2, 5, or 10 cM to at least one of the markers of (1) and (2) conferring resistance to FOM race 1,2; (b) crossing the *Cucumis melo* plant provided in step (a) with *Cucumis melo* culture breeding material to produce one or more progeny individuals, whereby one or more melon plants which are resistant to *F. oxysporum* f.sp. *melonis* (FOM) race 1,2 occurring in melon are produced. In some embodiments, the methods further comprise (c) collecting the seeds resulting from the cross in step (b); (d) regenerating the seeds into plants; (e) evaluating the plants of step (d) for resistance to FOM; and (f) identifying and selecting plants which are resistant to the FOM race 1,2. In some embodiments, the *Cucumis melo* plant provided in step (a) is 03MFR001795. In some embodiments, the FOM race 1,2 strain is a yellowing strain.

The presently disclosed subject matter also provides methods for producing seeds that result in melon plants resistant to FOM race 1,2 occurring in melon. In some embodiments, the methods comprise (a) providing a *Cucumis melo* plant which contains one or more alleles that confer resistance to FOM race 1,2, which alleles are characterized by one or more of five Quantitative Trait Loci QTL1-QTL5 on different chromosomes, wherein QTL1-QTL5 are as defined herein; (b) crossing the *Cucumis melo* plant provided in step (a) with *Cucumis melo* culture breeding material; and (c) collecting seeds resulting from the cross in step (b) that result in melon plants which are resistant to FOM, particularly FOM race 1,2.

The presently disclosed subject matter also provides methods for identifying a first *Cucumis melo* plant or germplasm that displays resistance, improved resistance, or reduced susceptibility to FOM race 1,2. In some embodiments, the methods comprise detecting in the first *Cucumis melo* plant or germplasm at least one allele of one or more marker locus that is associated with the resistance, improved resistance, or reduced susceptibility, wherein the one or more marker locus is selected from the group consisting of (a) 3.1, 3.2, 6.1, 6.2, 7.1, 7.2, 9.1, 9.2, 9.3, 10.1, and 10.2; (b) a marker locus linked to a marker locus of (a); and (c) a marker locus localizing within a chromosome interval including a marker pair selected from the group consisting of 3.1 and 3.2, 6.1 and 6.2, 7.1 and 7.2, 9.1 and 9.3, and 10.1 and 10.2. In some embodiments, the closely linked marker locus of (b) displays a genetic recombination frequency of less than about 10%, optionally, less than 5%, and further optionally less than about 1%, with the marker locus of (a). In some embodiments, the one or more marker locus associated with resistance, improved resistance, or reduced susceptibility is selected from the marker loci of (a) and (b). In some embodiments, the one or more marker locus associated with resistance, improved resistance, or reduced susceptibility is a plurality of loci selected from the marker loci of (a) and (b). In some embodiments, the one or more marker locus associated with resistance, improved resistance, or reduced susceptibility is selected from marker loci localizing within the chromosome intervals of (c). In some embodiments, the one or more marker locus associated with resistance, improved resistance, or reduced susceptibility is a plurality of loci selected from marker loci localizing within the chromosome intervals of (c). In some embodiments, the germplasm is a *Cucumis melo* line or variety. In some embodiments, the resistance, improved resistance, or reduced susceptibility to FOM race 1,2 is assayed in a field location previously known to produce *Cucumis melo* plants that demonstrate FOM race 1,2 infection. In some embodiments, the FOM race 1,2 is a yellowing strain. In some embodiments, the resistance, improved resistance, or reduced susceptibility further provides resistance, improved resistance, or reduced susceptibility to at least one of FOM races 0, 1, and 2. In some embodiments, the detecting comprises detecting at least one allelic form of a polymorphic simple sequence repeat (SSR) or a single nucleotide polymorphism (SNP). In some embodiments, the detecting comprises amplifying the marker, locus or a portion of the marker locus and detecting the resulting amplified marker amplicon. In some embodiments, the amplifying comprises: (a) admixing an amplification primer or amplification primer pair with a nucleic acid isolated from the first *Cucumis melo* plant or germplasm, wherein the primer or primer pair is complementary or partially complementary to at least a portion of the marker locus, and is capable of initiating DNA polymerization by a DNA polymerase using the melon nucleic acid as a template; and (b) extending the primer or primer pair in a DNA polymerization reaction comprising a DNA polymerase and a template nucleic acid to generate at least one amplicon. In some embodiments, the nucleic acid is selected from DNA and RNA. In some embodiments, the at least one allele is an SNP allele, the method comprising, detecting the SNP using allele specific hybridization (ASH) analysis. In some embodiments, the amplifying comprises employing a polymerase chain reaction (PCR) or ligase chain reaction (LCR) using a nucleic acid isolated from the first melon plant or germplasm as a template in the PCR or LCR. In some embodiments, the at least one allele is a favorable allele that positively correlates with resistance, improved resistance, or reduced susceptibility. In some embodiments, the at least one allele comprises two or more alleles. In some embodiments, the at least one allele is correlated with resistance, improved resistance, or reduced susceptibility to FOM race 1,2, the method comprising introgressing the allele in the first *Cucumis melo* plant or germplasm into a second *Cucumis melo* plant or germplasm to produce an introgressed *Cucumis melo* plant or germplasm. In some embodiments, the second *Cucumis melo* plant or germplasm displays less resistance to FOM race 1,2 infection as compared to the first *Cucumis melo* plant or germplasm, and wherein the introgressed *Cucumis melo* plant or germplasm displays an increased resistance, improved resistance, or reduced susceptibility to FOM race 1,2 infection as compared to the second *Cucumis melo* plant or germplasm.

The presently disclosed subject matter also provides quantitative trait loci (QTLs) associated with resistance to FOM race 1,2 in a melon. In some embodiments, the QTLs map to a linkage group in the melon genome selected from linkage group 3 mapped by one or more of the markers 3.1, 3.2, 3.3, and 3.4; linkage group 6 and mapped by one or more of the markers 6.1, 6.2, and 6.3; linkage group 7 and mapped by one or more of the markers 7.1, 7.2, and 7.3; linkage group 9 and mapped by one or more of the markers 9.1, 9.2, and 9.3; and linkage group 10 and mapped by one or more of the markers 10.1, 10.2, and 10.3.

The presently disclosed subject matter also provides isolated and purified genetic markers associated with FOM race 1,2 resistance in *Cucumis melo*. In some embodiments, the markers (a) map to a linkage group in a *Cucumis melo* genome, the linkage group selected from the group consisting of QTL1, QTL2, QTL3, QTL4, and QTL5; or (b) are selected from the group consisting of 3.1, 3.2, 6.1, 6.2, 7.1, 7.2, 9.1, 9.2, 9.3, 10.1, and 10.2; or (c) comprise a nucleotide sequence selected of at least 10 contiguous bases, optionally at least 15 contiguous bases, and also optionally the full length sequence of any of odd SEQ ID NOs: 1-21 or the complement of any of even SEQ ID NOs: 2-22; or (d) comprise a nucleotide sequence of at least 10 contiguous nucleotides contained within an amplification product from a DNA sample isolated from a melon, wherein the amplification product is produced by an amplification reaction using pairs of oligonucleotide primers comprising the following nucleotide sequences: SEQ ID NOs: 1 and 2; SEQ ID NOs: 3 and 4; SEQ ID NOs: 5 and 6; SEQ ID NOs: 7 and 8; SEQ ID NOs: 9 and 10; SEQ ID NOs: 11 and 12; SEQ ID NOs: 13 and 14; SEQ ID NOs: 15 and 16; SEQ ID NOs: 17 and 18; SEQ ID NOs: 19 and 20; or SEQ ID NOs: 21 and 22. In some embodiments, the probe comprises an isolated and purified genetic marker as disclosed herein and a detectable moiety.

The presently disclosed subject matter also provides improved melon plants, seeds, and tissue cultures produced by any of the presently disclosed methods.

The presently disclosed subject matter also provides improved melon plants or a part thereof, which evidences a resistance response to *F. oxysporum* f.sp. melonis (FOM) race 1,2, comprising a genome homozygous with respect to one or more genetic alleles which are native to a first parent and non-native to a second parent of the improved melon plant. In some embodiments, (a) the second parent evidences less resistance response to FOM race 1,2 than the first parent; and (b) the improved plant comprises one or more alleles from the first parent that evidence resistance to FOM race 1,2 in hybrid combination in at least one locus selected from (i) a locus mapping to linkage group 3 and mapped by one or more of the markers 3.1 and 3.2; (ii) a locus mapping to linkage group 6 and mapped by one or more of the markers 6.1 and 6.2; (iii) a locus mapping to linkage group 7 and mapped by one or more of the markers 7.1 and 7.2; (iv) a locus mapping to linkage group 9 and mapped by one or more of the markers 9.1, 9.2, and 9.3; and (v) a locus mapping to linkage group 10 and mapped by one or so more of the markers 10.1 and 10.2; the resistance is not significantly less than that of the first parent in the same hybrid combination and yield characteristics which are not significantly different than those of the second parent in the same hybrid combination. In some embodiments, the improved melon plants comprise each of (a) a locus mapping to linkage group 3 and mapped by one or more of the markers 3.1 and 3.2; and (b) a locus mapping to linkage group 9 and mapped by one or more of the markers 9.1, 9.2, and 9.3; and have improved resistance to FOM race 1,2 when compared to a substantially identical melon plant not comprising the loci. In some embodiments, the improved melon plants or parts thereof comprise progeny of a cross between first and second inbred or hybrid lines, wherein one or more alleles conferring resistance to FOM race 1,2 are present in a homozygous state in the genome of one or the other or both of the first and second inbred or hybrid lines, such that the genome of the first and second inbreds or hybrids together donate to the improved melon plant or part thereof a complement of alleles sufficient to confer the resistance to FOM race 1,2. In some embodiments, the improved melon plants or parts thereof have orange flesh.

The presently disclosed subject matter also provides FOM race 1,2-resistant hybrids, or a part thereof, formed with the presently disclosed improved melon plants.

The presently disclosed subject matter also provides melon plants, or a part thereof, formed by selling the presently disclosed FOM race 1,2-resistant hybrids.

The presently disclosed subject matter also provides melon plants that are resistant to FOM race 1,2 occurring in melon produced by the presently disclosed methods. In some embodiments, the melon plants that are resistant to FOM race 1,2 occurring in melon are hybrid melons.

The presently disclosed subject matter also provides fruit and seed produced by the presently disclosed melon plants. In some embodiments, the seed the seed comprises a melon line referred to herein as 03MFR001795 and corresponding to the seed deposited with NCIMB Ltd. under the terms of the Budapest Treaty on 27 Apr. 2007 as Accession No. 41478, or an ancestor or descendent thereof.

The presently disclosed subject matter also provides introgressed *Cucumis melo* plants or germplasm produced by the presently disclosed methods. In some embodiments, the introgressed *Cucumis melo* plants and/or germplasm are homozygous for orange flesh.

The presently disclosed subject matter also provides compositions comprising amplification primer pairs capable of initiating DNA polymerization by a DNA polymerase on *Cucumis melo* nucleic acid templates to generate *Cucumis melo* marker amplicons. In some embodiments, the *Cucumis melo* marker amplicons correspond to *Cucumis melo* markers 3.1, 3.2, 6.1, 6.2, 7.1, 7.2, 9.1, 9.2, 9.3, 10.1, or 10.2. In some embodiments, the amplification primer pairs comprise one or more nucleotide sequence pairs selected from the group consisting of SEQ ID NOs: 1 and 2; SEQ ID NOs: 3 and 4; SEQ ID NOs: 5 and 6; SEQ ID NOs: 7 and 8; SEQ ID NOs: 9 and 10; SEQ ID NOs: 11 and 12; SEQ ID NOs: 13 and 14; SEQ ID NOs: 15 and 16; SEQ ID NOs: 17 and 18; SEQ ID NOs: 19 and 20; and SEQ ID NOs: 21 and 22.

The presently disclosed subject matter also provides *Cucumis melo* plants having improved FOM-1,2 resistance associated with the presence of QTL4 as defined herein in an homozygous orange flesh genetic background.

The presently disclosed subject matter also provides melon plants that are resistant to FOM race 1,2, wherein the plant is a plant of the species *Cucumis melo*, and the plant comprises at least one chromosomal region that confers FOM race 1,2 resistance, and further wherein the at least one chromosomal region that confers FOM race 1,2 resistance is linked to at least one marker selected from the group consisting of markers 3.1, 3.2, 6.1, 6.2, 7.1, 7.2, 9.1, 9.2, 9.3, 10.1, or 10.2. In some embodiments, the melon plant is homozygous for a chromosomal region that confers FOM race 1,2 resistance linked to marker 9.1, 9.2, or 9.3, or a combination thereof. In some embodiments, the melon plant is homozygous for orange flesh.

The presently disclosed subject matter also provides parts of the plants defined herein. In some embodiments, the plant part is selected from the group consisting of pollen, ovule, leaf, embryo, root, root tip, anther, flower, fruit, stem, shoot, seed; scion, rootstock, protoplast, and callus.

Thus, it is an object of the presently disclosed subject matter to provide methods for conveying FOM race 1,2 resistance into non-resistant melon germplasm.

An object of the presently disclosed subject matter having been stated hereinabove, and which is achieved in whole or in part by the presently disclosed subject matter, other objects will become evident as the description proceeds when taken in connection with the accompanying drawings as best described hereinbelow.

BRIEF DESCRIPTION OF THE SEQUENCE LISTING

SEQ ID NOs: 1 and 2 are the nucleotide sequences of oligonucleotides that can be employed together to amplify marker 3.1 associated with QTL1 on chromosome 3.

SEQ ID NOs: 3 and 4 are the nucleotide sequences of oligonucleotides that can be employed together to amplify marker 3.2 associated with QTL1 on chromosome 3.

SEQ ID NOs: 5 and 6 are the nucleotide sequences of oligonucleotides that can be employed together to amplify marker 6.1 associated with QTL2 on chromosome 6.

SEQ ID NOs: 7 and 8 are the nucleotide sequences of oligonucleotides that can be employed together to amplify marker 6.2 associated with QTL2 on chromosome 6.

SEQ ID NOs: 9 and 10 are the nucleotide sequences of oligonucleotides that can be employed together to amplify marker 7.1 associated with QTL3 on chromosome 7.

SEQ ID NOs: 11 and 12 are the nucleotide sequences of oligonucleotides that can be employed together to amplify marker 7.2 associated with QTL3 on chromosome 7.

SEQ ID NOs: 13 and 14 are the nucleotide sequences of oligonucleotides that can be employed together to amplify marker 9.1 associated with QTL4 on chromosome 9.

SEQ ID NOs: 15 and 16 are the nucleotide sequences of oligonucleotides that can be employed together to amplify marker 9.2 associated with QTL4 on chromosome 9.

SEQ ID NOs: 17 and 18 are the nucleotide sequences of oligonucleotides that can be employed together to amplify marker 9.3 associated with QTL4 on chromosome 9.

SEQ ID NOs: 19 and 20 are the nucleotide sequences of oligonucleotides that can be employed together to amplify marker 10.1 associated with QTL5 on chromosome 10.

SEQ ID NOs: 21 and 22 are the nucleotide sequences of oligonucleotides that can be employed together to amplify marker 10.2 associated with QTL5 on chromosome 10.

SEQ ID NO: 23 is a 17 nucleotide sequence derived from M13 that can be placed as a tag (in some embodiments, a fluorescently-labeled tag) 5' to nucleotide 1 of any of odd-numbered SEQ ID NOs: 1-21 to aid in the determination using a sequencer of the size of the amplification fragment that is produced when oligonucleotides comprising these sequences are employed to amplify DNA or RNA extracted from a hybrid or inbred *Cucumis melo* plant or part thereof.

DETAILED DESCRIPTION

The presently disclosed subject matter relates at least in part to the identification of one or more quantitative trait loci associated with *Fusarium oxysporum* f.sp. melonis (FOM) race 1,2 resistance in *Cucumis melo*. Thus, provided herein are methods of conveying FOM race 1,2 resistance into non-resistant melon germplasm, which employ one or more of the identified quantitative trait loci in various approaches.

The presently disclosed subject matter also relates at least in part to the generation of a recombination event through which a linkage of green flesh and a particular QTL associated with *Fusarium oxysporum* f.sp. *melonis* (FOM) race 1,2 resistance in *Cucumis melo* has been broken. Thus, provided in accordance with the presently disclosed subject matter is a *Cucumis melo* plant having improved FOM race 1,2 resistance in a homozygous orange flesh genetic background.

I. DEFINITIONS

While the following terms are believed to be well understood by one of ordinary skill in the art, the following definitions are set forth to facilitate explanation of the presently disclosed subject matter.

Unless defined otherwise, all technical and scientific terms used herein have the same meaning as commonly understood to one of ordinary skill in the art to which the presently disclosed subject matter belongs. Although any methods, devices, and materials similar or equivalent to those described herein can be used in the practice or testing of the presently disclosed subject matter, representative methods, devices, and materials are now described.

Following long-standing patent law convention, the articles "a", "an", and "the" refer to "one or more" when used in this application, including in the claims. For example, the phrase "a marker" refers to one or more markers. Similarly, the phrase "at least one", when employed herein to refer to an entity, refers to, for example, 1, 2, 3, 4, 5, 6, 7, 8, 9, 10, 15, 20, 25, 30, 35, 40, 45, 50, 75, 100, or more of that entity, including but not, limited to whole number values between 1 and 100 and greater than 100.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in this specification and attached claims are approximations that can vary depending upon the desired properties sought to be obtained by the presently disclosed subject matter.

As used herein, the term "about," when referring to a value or to an amount of mass, weight, time, volume, concentration or percentage is meant to encompass variations of in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed method.

As used herein, the term "allele" refers to any of one or more alternative forms of a gene, all of which relate, to at least one trait or characteristic. In a diploid cell, two alleles of a given gene occupy corresponding loci on a pair of homologous chromosomes, although one of ordinary skill in the art understands that the alleles in any particular individual do not necessarily represent all of the alleles that are present in the species. Since the presently disclosed subject matter relates to QTLs (i.e., genomic regions that can comprise one or more genes or regulatory sequences), it is in some instances more accurate to refer to a "haplotype" (i.e., an allele of a chromosomal segment) instead of "allele". However, in such instances, the term "allele" should be understood to comprise the term "haplotype".

As used herein, the phrase "associated with" refers to a recognizable and/or assayable relationship between two entities. For example, the phrase "associated with resistance" refers to a trait, locus, QTL, gene, marker, phenotype, etc., or the expression thereof, the presence or absence of which influences an extent or degree of resistance (e.g., resistance to FOM race 1,2).

As used herein, the term "backcross", and grammatical variants thereof, refers to a process in which a breeder crosses a hybrid progeny back to one of the parents, for example, a first generation hybrid F1 with one of the parental genotypes of the F1 hybrid. In some embodiments, a backcross is performed repeatedly, with a progeny individual of one backcross being itself backcrossed to the same parental genotype.

The term "chromosome" is used herein in its art-recognized meaning of the self-replicating genetic structure in the cellular nucleus containing the cellular DNA and bearing in its nucleotide sequence the linear array of genes. The *Cucumis melo* chromosome numbers disclosed herein refer to those as set forth in Perin et al., 2002, which relates to a reference nomenclature system adopted by L'institut National de la Recherchë Agronomique (INRA; Paris, France).

As used herein, the terms "cultivar" and "variety" refer to a group of similar plants that by structural or genetic features and/or performance can be distinguished from other varieties within the same species.

As used herein, the term "gene" refers to a hereditary unit including a sequence of DNA that occupies a specific location on a chromosome and that contains the genetic instruction for a particular characteristics or trait in an organism.

As used herein, the term "heterozygous" refers to a genetic condition existing when different alleles reside at corresponding loci on homologous chromosomes.

As used herein, the term "homozygous" refers to a genetic condition existing when identical alleles reside at corresponding loci on homologous chromosomes.

As used herein, the term "hybrid" in the context of nucleic acids refers to a double-stranded nucleic acid molecule, or duplex, formed by hydrogen bonding between complementary nucleotide bases. The terms "hybridize" or "anneal" refer to the process by which single strands of nucleic acid sequences form double-helical segments through hydrogen bonding between complementary bases.

As used herein, the term "hybrid" in the context of plant breeding refers to a plant that is the offspring of genetically dissimilar parents produced by crossing plants of different lines or breeds or species, including but not limited to the cross between two inbred lines.

As used herein, the term "inbred" refers to a substantially homozygous individual or line.

As used herein, the terms "introgression", "introgressed", and "introgressing" refer to both a natural and artificial process whereby genomic regions of one species, variety, or cultivar are moved into the genome of another species, variety, or cultivar, by crossing those species. The process can optionally be completed by backcrossing to the recurrent parent.

As used herein, the term "linkage" refers to a phenomenon wherein alleles on the same chromosome tend to be transmitted together more often than expected by chance if their transmission was independent. Thus, two alleles on the same chromosome are said to be "linked" when they segregate from each other in the next generation in some embodiments less than 50% of the time, in some embodiments less than 25% of the time, in some embodiments less than 20% of the time, in some embodiments less than 15% of the time, in some embodiments less than 10% of the time, in some embodiments less than 9% of the time, in some embodiments less than 8% of the time, in some embodiments less than 7% of the time, in some embodiments less than 6% of the time, in some embodiments less than 5% of the time, in some embodiments less than 4% of the time, in some embodiments less than 3% of the time, in some embodiments less than 2% of the time, and in some embodiments less than 1% of the time.

In some embodiments, "linkage" implies physical proximity on a chromosome. Thus, two loci are linked if they are within in some embodiments 20, in some embodiments 15, in some embodiments 12, in some embodiments 10, in some embodiments 9, in some embodiments 8, in some embodiments 7, in some embodiments 6, in some embodiments 5, in some embodiments 4, in some embodiments 3, in some embodiments 2, and in some embodiments 1 centiMorgans (cM) of each other. Similarly, a QTL is linked to a marker if it is in some embodiments within 20, 15, 12, 10, 9, 8, 7, 6, 5, 4, 3, 2, or 1 cM of the marker.

As used herein, the phrase "linkage group" refers to all of the genes or genetic traits that are located on the same chromosome. Within the linkage group, those loci that are close enough together can exhibit linkage in genetic crosses. Since the probability of crossover increases with the physical distance between loci on a chromosome, loci for which the locations are far removed from each other within a linkage group might not exhibit any detectable linkage in direct genetic tests. The term "linkage group" is mostly used to refer to genetic loci that exhibit linked behavior in genetic systems where chromosomal assignments have not yet been made. Thus, in the present context, the term "linkage group" is synonymous with the physical entity of a chromosome, although one of ordinary skill in the art will understand that a linkage group can also be defined as corresponding to a region of (i.e., less than the entirety) of a given chromosome.

As used herein, the term "locus" refers to a position that a given gene or a regulatory sequence occupies on a chromosome of a given species.

As used herein, the term "marker" refers to an identifiable position on a chromosome the inheritance of which can be monitored. In some embodiments, a marker comprises a known or detectable nucleic acid sequence.

In some embodiments, a marker corresponds to an amplification product generated by amplifying a *Cucumis melo* nucleic acid with two oligonucleotide primers, for example, by the polymerase chain reaction (PCR). As used herein, the phrase "corresponds to an amplification product" in the context of a marker refers to a marker that has a nucleotide sequence that is the same (allowing for mutations introduced by the amplification reaction itself) as an amplification product that is generated by amplifying *Cucumis melo* genomic DNA with a particular set of primers. In some embodiments, the amplifying is by PCR, and the primers are PCR primers that are designed to hybridize to opposite strands of the *Cucumis melo* genomic DNA in order to amplify a *Cucumis melo* genomic DNA sequence present between the sequences to which the PCR primers hybridize in the *Cucumis melo* genomic DNA. The amplified fragment that results from one or more rounds of amplification using such an arrangement of primers is a double stranded nucleic acid, one strand of which has a nucleotide sequence that comprises, in 5' to 3' order, the sequence of one of the primers', the sequence of the *Cucumis melo* genomic DNA located between the primers, and the reverse-complement of the second primer. Typically, the "forward" primer is assigned to be the primer that has the same sequence as a subsequence of the (arbitrarily assigned) "top" strand of a double-stranded nucleic acid to be amplified, such that the "top" strand of the amplified fragment includes a nucleotide sequence that is, in 5' to 3' direction, equal to the sequence of the forward primer—the sequence located between the forward and reverse primers of the top strand, of the genomic fragment—the reverse-complement of the reverse primer. Accordingly, a marker that "corresponds to" an amplified fragment is a marker that has the same sequence of one of the strands of the amplified fragment.

As used herein, the term "melon" refers to a plant, or a part thereof, of the species *Cucumis melo*, also referred to herein as *Cucumis melo* L.

As used herein, the phrase "melon-specific DNA sequence" refers to a polynucleotide sequence having a nucleotide sequence homology of in some embodiments more than 50%, in some embodiments more than 55%, in some embodiments more than 60%, in some embodiments more than 65%, in some embodiments more than 70%, in some embodiments more than 75%, in some embodiments more than 80%, in some embodiments more than 85%, in some embodiments more than 90%, in some embodiments more than 92%, in some embodiments more than 95%, in some embodiments more than 96%, in some embodiments more than 97%, in some embodiments more than 98%, and in some embodiments more than 99% with a sequence of the genome of the species *Cucumis melo* that shows the greatest similarity to it, in some embodiments in the case of markers for any of QTL1-QTL5, the part of the DNA sequence of a melon flanking the QTL1-QTL5 markers.

As used herein, the phrase "molecular marker" refers to an indicator that is used in methods for visualizing differences in characteristics of nucleic acid sequences. Examples of such indicators are restriction fragment length polymorphism (RFLP) markers, amplified fragment length polymorphism (AFLP) markers, single nucleotide polymorphisms (SNPs), insertion mutations, microsatellite markers (SSRs), sequence-characterized amplified regions (SCARS), cleaved amplified polymorphic sequence (CAPS) markers or isozyme markers or combinations of the markers described herein which defines a specific genetic and chromosomal location. A "molecular marker linked to a QTL" as defined herein can thus refer to SNPs, insertion mutations, as well as more usual AFLP markers or any other type of marker used in the field.

As used herein, the phrase "nucleotide sequence homology" refers to the presence of homology between two polynucleotides. Polynucleotides have "homologous" sequences if the sequence of nucleotides in the two sequences is the same when aligned for maximum correspondence. Sequence comparison between two or more polynucleotides is generally performed by comparing portions of the two sequences over a comparison window to identify and compare local regions of sequence similarity. The comparison window is generally from about 20 to 200 contiguous nucleotides. The "percentage of sequence homology" for polynucleotides, such as 50, 60, 70, 80, 90, 95, 98, 99 or 100 percent sequence homology can be determined by comparing two optimally aligned sequences over a comparison window, wherein the portion of the polynucleotide sequence in the comparison window may include additions or deletions (i.e., gaps) as compared to the reference sequence (which does not comprise additions or deletions) for optimal alignment of the two sequences. The percentage is calculated by: (a) determining the number of positions at which the identical nucleic acid base occurs in both sequences to yield the number of matched positions; (b) dividing the number of matched positions by the total number of positions in the window of comparison; and (c) multiplying the result by 100 to yield the percentage of sequence homology. Optimal alignment of sequences for comparison may be conducted by computerized implementations of known algorithms, or by visual inspection. Readily available sequence comparison and multiple sequence alignment algorithms are, respectively, the Basic Local Alignment Search Tool (BLAST; Altschul et al., 1990; Altschul et al., 1997) and ClustalW programs, both available on the internet. Other suitable programs include, but are not limited to, GAP, BestFit, PlotSimilarity, and FASTA, which are part of the Accelrys GCG Package available from Accelrys, Inc. of San Diego, Calif., United States of America.

As used herein, the term "offspring" plant refers to any plant resulting as progeny from a vegetative or sexual reproduction from one or more parent plants or descendants thereof. For instance an offspring plant can be obtained by cloning or setting of a parent plant or by crossing two parent plants and include selfings as well as the F1 or F2 or still further generations. An F1 is a first-generation offspring produced from parents at least one of which is used for the first time as donor of a trait, while offspring of second generation (F2) or subsequent generations (F3, F4, and the like.) are specimens produced from selfings of F1s, F2s and the like. An F1 can thus be (and in some embodiments is) a hybrid resulting from a cross between two true breeding parents (true-breeding is homozygous for a trait), while an F2 can be (and in some embodiments is) an offspring resulting from self-pollination of the F1 hybrids.

As used herein, the term "phenotype" refers to a detectable characteristic of a cell or organism, which characteristics are at least partially a manifestation of gene expression.

As used herein, the phrase "plant part" refers to a part of a plant, including single cells and cell tissues such as plant cells that are intact in plants, cell clumps, and tissue cultures from which plants can be regenerated. Examples of plant parts include, but are not limited to, single cells and tissues from pollen, ovules, leaves, embryos, roots, root tips, anthers, flowers, fruits, stems, shoots, and seeds; as well as scions, rootstocks, protoplasts, calli, and the like.

As used herein, the term "population" refers to a genetically heterogeneous collection of plants sharing a common genetic derivation.

As used herein, the term "primer" refers to an oligonucleotide which is capable of annealing to a nucleic acid target allowing a DNA polymerase to attach, thereby serving as a point of initiation of DNA synthesis when placed under conditions in which synthesis of a primer extension product is induced (e.g., in the presence of nucleotides and an agent for polymerization such as DNA polymerase and at a suitable temperature and pH).

The primer (in some embodiments an extension primer and in some embodiments an amplification primer) is in some embodiments single stranded for maximum efficiency in extension and/or amplification. In some embodiments, the primer is an oligodeoxyribonucleotide.

A primer is typically sufficiently long to prime the synthesis of extension and/or amplification products in the presence of the agent for polymerization. The minimum lengths of the primers can depend on many factors, including, but not limited to temperature and composition (A/T vs. G/C content) of the primer.

In the context of an amplification primer, these are typically provided as a pair of bi-directional primers consisting of one forward and one reverse primer as commonly used in the art of DNA amplification such as in PCR amplification.

As such, it will be understood that the term "primer", as used herein, can refer to more than one primer, particularly in the case where there is some ambiguity in the information regarding the terminal sequence(s) of the target region to be amplified. Hence, a "primer" can include a collection of primer oligonucleotides containing sequences representing the possible variations in the sequence or includes nucleotides which allow a typical base pairing.

Primers can be prepared by any suitable method. Methods for preparing oligonucleotides of specific sequence are known in the art, and include, for example, cloning and restriction of appropriate sequences and direct chemical synthesis. Chemical synthesis methods can include, for example, the phospho di- or tri-ester method, the diethylphosphoramidate method and the solid support method disclosed in U.S. Pat. No. 4,458,066.

Primers can be labeled, if desired, by incorporating detectable moieties by for instance spectroscopic, fluorescence, photochemical, biochemical, immunochemical, or chemical moieties.

Template-dependent extension of an oligonucleotide primer is catalyzed by a polymerizing agent in the presence of adequate amounts of the four deoxyribonucleotide triphosphates (dATP, dGTP, dCTP and dTTP; i.e., dNTPs) or analogues, in a reaction medium that comprises appropriate salts, metal cations, and a pH buffering system. Suitable polymerizing agents are enzymes known to catalyze primer- and template-dependent DNA synthesis. Known DNA polymerases include, for example, *E. coli* DNA polymerase I or its Klenow fragment, T4 DNA polymerase, and Taq DNA polymerase, as well as various modified versions thereof. The reaction conditions for catalyzing DNA synthesis with these DNA polymerases are known in the art. The products of the synthesis are duplex molecules consisting of the template strands and the primer extension strands, which include the target sequence. These products, in turn, can serve as template for another round of replication. In the second round of replication, the primer extension strand of the first cycle is annealed with its complementary primer; synthesis yields a "short" product which is bound on both the 5'- and the 3'-ends by primer sequences or their complements. Repeated cycles of denaturation, primer annealing, and extension result in the exponential accumulation of the target region defined by the primers. Sufficient cycles are run to achieve the desired amount of polynucleotide containing the target region of nucleic acid. The desired amount can vary, and is determined by the function which the product polynucleotide is to serve.

The PCR method is well described in handbooks and known to the skilled person. After amplification by PCR, the target polynucleotides can be detected by hybridization with a probe polynucleotide which forms a stable hybrid with that of the target sequence under stringent to moderately stringent hybridization and wash conditions. If it is expected that the probes will be essentially completely complementary (i.e., about 99% or greater) to the target sequence, stringent conditions can be used. If some mismatching is expected, for example if variant strains are expected with the result that the probe will not be completely complementary, the stringency of hybridization can be reduced. In some embodiments, conditions are chosen to rule out non-specific/adventitious binding. Conditions that affect hybridization, and that select against non-specific binding are known in the art, and are described in, for example, Sambrook & Russell, 2001. Generally, lower salt concentration and higher temperature increase the stringency of hybridization conditions.

Continuing, the term "probe" refers to a single-stranded oligonucleotide sequence that will form a hydrogen-bonded duplex with a complementary sequence in a target nucleic acid sequence analyte or its cDNA derivative.

As used herein, the terms "QTL1", "QTL2", "QTL3", "QTL4", and "QTL5" refer to the genomic regions linked to FOM race 1,2 resistance as defined by the markers 3.1 and 3.2; 6.1 and 6.2; 7.1 and 7.2; 9.1, 9.2, and 9.3; and 10.1 and 10.2; respectively. For the purposes of the instant disclosure, these markers are said to be present on *Cucumis melo* chromosomes 3, 6, 7, 9, and 10, respectively.

As used herein, the term "quantitative trait locus" (QTL; plural quantitative trait loci; QTLs) refers to a genetic locus (or loci) that control to some degree a numerically representable trait that, in some embodiments, is continuously distributed. As such, the term QTL is used herein in its art-recognized meaning to refer to a chromosomal region containing alleles (e.g., in the form of genes or regulatory sequences) associated with the expression of a quantitative phenotypic trait. Thus, a QTL "associated with" resistance to FOM race 1,2 refers to one or more regions located on one or more chromosomes that includes at least one gene the expression of which influences a level of resistance and/or at least one regulatory region that controls the expression of one or more genes involved in resistance to FOM race 1,2. The QTLs can be defined by indicating their genetic location in the genome of a specific *Cucumis melo* accession using one or more molecular genomic markers. One or more markers, in turn, indicate a specific locus. Distances between loci are usually measured by the frequency of crossovers between loci on the same chromosome. The farther apart two loci are, the more likely that a crossover will occur between them. Conversely, if two loci are close together, a crossover is less likely to occur between them. Typically, one centiMorgan 1.5 (CM) is equal to 1% recombination between loci. When a QTL can be indicated by multiple markers, the genetic distance between the end-point markers is indicative of the size of the QTL.

As used herein, the term "recombination" refers to an exchange (a "crossover") of DNA fragments between two DNA molecules or chromatids of paired chromosomes over in a region of similar or identical nucleotide sequences. A "recombination event" is herein understood to refer to a meiotic crossover.

As used herein, the term "regenerate", and grammatical variants thereof, refers to the production of a plant from tissue culture.

As used herein, the term "resistant" and "resistance" encompass both partial and full resistance to infection (e.g., infection by FOM race 1,2). A susceptible plant can either be non-resistant or have lower levels of resistance to infection relative to a resistant plant. The term is used to include such separately identifiable forms of resistance as "full resistance", "immunity", "intermediate resistance", "partial resistance", "hypersensitivity", and "tolerance".

As used herein, the phrase "stringent hybridization conditions" refers to conditions under which a polynucleotide hybridizes to its target subsequence, typically in a complex mixture of nucleic acids, but to essentially no other sequences. Stringent conditions are sequence-dependent and can be different under different circumstances. Longer sequences hybridize specifically at higher temperatures. An extensive guide to the hybridization of nucleic acids is found in Tijssen, 1993. Generally, stringent conditions are selected to be about 5-10° C. lower than the thermal melting point (Tm) for the specific sequence at a defined ionic strength pH. The Tm is the temperature (under defined ionic strength, pH, and nucleic acid concentration) at which 50% of the probes complementary to the target hybridize to the target sequence at equilibrium (as the target sequences are present in excess, at Tm, 50% of the probes are occupied at equilibrium). Stringent conditions are those in which the salt concentration is less than about 1:0 M sodium ion, typically about 0.01 to 1.0 M sodium ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions can also be achieved with the addition of destabilizing agents such as formamide. For selective or specific hybridization, a positive signal is in some embodiments at least two times background, and in some embodiments 10 times background hybridization. Exemplary stringent hybridization conditions include: 50% formamide, 5×SSC, and 1% SDS, incubating at 42° C.; or 5×SSC, 1% SOS, incubating at 65° C.; with one or more washes in 0.2×SSC and 0.1% SDS at 65° C. For PCR, a temperature of about 36° C. is typical for low stringency amplification, although annealing temperatures can vary between about 32° C. and 48° C. (or higher) depending on primer length. Additional guidelines for determining hybridization parameters are provided in numerous references (see e.g., Ausubel et al., 1999).

As used herein, the term "susceptible" refers to a plant having no resistance to the disease resulting in the plant being affected by the disease, resulting in disease symptoms. The term "susceptible" is therefore equivalent to "non-resistant". Alternatively, the term "susceptible" can be employed in a relative context, in which one plant is considered "susceptible" because it is less resistant to a particular pathogen than is a second plant (which in the context of these terms in a relative usage, would be referred to as the "resistant" plant").

II. PLANT BREEDING

The purpose of breeding programs in agriculture and horticulture is to enhance the performances of plants by improving their genetic composition. In essence, this improvement accrues by increasing the frequency of the most favorable alleles for the genes influencing the performance characteristics of interest. Wild plant lines provide a rich resource of genetic and phenotypic variation. Traditionally, agricultural or horticultural practice makes use of this variation by selecting a wild plant line or its offspring for having desired genotypic or potential phenotypic properties, crossing it with a line having additional desired genotypic or potential phenotypic properties and selecting from among the offspring plants those that exhibit the desired genotypic or potential phenotypic properties (or an increased frequency thereof).

A growing understanding and utilization of the laws of Mendelian inheritance in combination with molecular genetic tools have in the past century facilitated this selection process. For example, methods for selecting plants for having desired genotypic or potential phenotypic properties have become available based on testing the plant for the presence of a quantitative trait locus (QTL); i.e., for the presence of a chromosomal region containing alleles associated with the expression of a continuously distributed (quantitative) phenotypic trait. Usually a QTL is characterized by one or more markers that statistically associate to the quantitative variation in the phenotypic trait and is essentially synonymous to a gene. QTL mapping allows for the identification of candidate loci affecting the expression of a trait of interest. In plant breeding, it allows for marker-assisted selection (MAS); i.e., the selection of plants having favorable alleles by detecting in those plants the QTL-associated markers.

One of the major problems in breeding programs of cultivated plants is the existence of negative genetic correlation between separate traits. This is for example the case with the negative genetic correlation between reproductive capacity and production in various disease-resistant plant lines. Understanding emerges to show that introgressions of DNA from the genome of one plant line into another can interfere with and/or otherwise negatively affect the expression of basic reproductive traits. Likewise, attempts to introgress resistance-conferring gene sequences from one plant into another can remove resistance traits already present in the recipient line.

Knowledge of the inheritance of various traits allows for the selection of lines homozygous for a QTL associated with disease resistance. Use of the knowledge of the genetic origin and location of a desired trait in a breeding program can increase the accuracy of the predicted breeding outcome and can enhance the rate of selection compared to conventional breeding programs. For instance, the fact that the genetic basis of a desired trait is heritably linked to another trait can help to increase uniformity for those two traits among the offspring since a parent homozygous for the desired alleles will pass them to most if not all offspring, resulting in a reduced segregation in the offspring.

The presently disclosed subject matter provides for better models for marker-assisted selection (MAS). The presently disclosed subject matter therefore relates to methods of plant breeding and to methods to select plants, in particular melon plants, particularly cultivated melon plants as breeder plants for use in breeding programs or cultivated melon plants for having desired genotypic or potential phenotypic properties, in particular related to producing valuable melons, also referred to herein as commercially valuable plants. Herein, a cultivated plant is defined as a plant being purposely selected or having been derived from a plant having been purposely selected in agricultural or horticultural practice for having desired genotypic or potential phenotypic properties, for example a plant obtained by inbreeding.

The presently disclosed subject matter thus also provides methods for selecting a plant of the species. *Cucumis melo* exhibiting resistance towards FOM race 1,2 comprising detecting in the plant the presence of one or more of QTL1-QTL5 as defined herein. In an exemplary embodiment of the presently disclosed methods for selecting such a plant, the method comprises providing a sample of genomic DNA from a melon plant; and (b) detecting in the sample of genomic DNA at least one molecular marker linked to a QTL selected from the group consisting of QTL1-QTL5. In some embodiments, the detecting can comprise detecting at least two molecular markers from the group, the at least two molecular markers detecting at least two (e.g., 2, 3, 4, or 5) of QTL1-QTL5.

The providing of a sample of genomic DNA from a melon plant can be performed by standard DNA isolation methods well known in the art.

The detecting of a molecular marker can in some embodiments comprise the use of one or more sets of primer pairs that can be used to produce one or more amplification products that are suitable markers for one of the QTLs. Such a set of primers can comprise, in some embodiments, nucleotide sequences as set forth in SEQ ID NOs: 1-22.

In some embodiments, the detecting of a molecular marker (step b) can comprise the use of a nucleic acid probe having a base sequence that is substantially complementary to the nucleic acid sequence defining the molecular marker and which nucleic acid probe specifically hybridizes under stringent conditions with a nucleic acid sequence defining the molecular marker. A suitable nucleic acid probe can for instance be a single strand of the amplification product corresponding to the marker.

The detecting of a molecular marker can also comprise the performance of a nucleic acid amplification reaction on the genomic DNA to detect one or more QTLs. This can be done by performing a PCR reaction using a set of marker-specific primers. In some embodiments, the detecting can comprise the use of at least one set of primers defining one or more markers linked to one or more of QTL1-QTL5, or a set of primers which specifically hybridize under stringent conditions with nucleic acid sequences of one or more markers linked to one or more of QTL1-QTL5.

The presently disclosed methods can also include detecting an amplified DNA fragment associated with the presence of a QTL. In some embodiments, the amplified fragment associated with presence of a QTL has a predicted length or nucleic acid sequence, and detecting an amplified DNA fragment having the predicted length or the predicted nucleic acid sequence is performed such that the amplified DNA fragment has a length that corresponds (plus or minus a few bases; e.g., a length of one, two or three bases more or less) to the expected length as based on a similar reaction with the same primers with the DNA from the plant in which the marker was first detected or the nucleic acid sequence that corresponds (has a homology of in some embodiments more than 80%, in some embodiments more than 90%, in some embodiments more than 95%, in some embodiments more than 97%, and in some embodiments more than 99%) to the expected sequence as based on the sequence of the marker associated with that QTL in the plant in which the marker was first detected. Upon a review of the instant disclosure, one of ordinary skill in the art would appreciate that markers that are absent in resistant plants, while they were present in the susceptible parent(s) (so-called trans-markers), can also be useful in assays for detecting resistance among offspring plants, although testing the absence of a marker to detect the presence of a specific trait is not optimal.

The detecting of an amplified DNA fragment having the predicted length or the predicted nucleic acid sequence can be performed by any of a number or techniques, including but not limited to standard gel-electrophoresis techniques or by using automated DNA sequencers. The methods are not described here in detail as they are well known to the skilled person, although exemplary approaches are set forth in EXAMPLES 5 and 6.

In order to detect in a plant the presence of two QTLs on a single chromosome, chromosome painting methods can also be used. In such methods at least a first QTL and at least a second QTL can be detected in the same chromosome by in situ hybridization or in situ PCR techniques. More conveniently, the fact that two QTLs are present on a single chromosome can be confirmed by determining that they are in coupling phase; i.e., that the traits show reduced segregation when compared to genes residing on separate chromosomes.

III. MOLECULAR MARKERS AND QTLs

Molecular markers are used for the visualization of differences in nucleic acid sequences. This visualization can be due to DNA-DNA hybridization techniques after digestion with a restriction enzyme (RFLP) and/or due to techniques using the polymerase chain reaction (e.g., STS, SSR/microsatellites, AFLP, and the like.). In some embodiments, all differences between two parental genotypes segregate in a mapping population based on the cross of these parental genotypes. The segregation of the different markers can be compared and recombination frequencies can be calculated. Methods for mapping markers in plants are disclosed in, for example, Glick & Thompson, 1993; Zietkiewicz et al., 1994.

The recombination frequencies of molecular markers on different chromosomes are generally 50%. Between molecular markers located on the same chromosome, the recombination frequency generally depends on the distance between the markers. A low recombination frequency corresponds to a low genetic distance between markers on a chromosome. Comparing all recombination frequencies results in the most logical order of the molecular markers on the chromosomes. This most logical order can be depicted in a linkage map (Paterson, 1996). A group, of adjacent or contiguous markers on the linkage map that is associated with an increased level of resistance to a disease; e.g., to a reduced incidence of acquiring the disease upon infectious contact with the disease agent and/or a reduced lesion growth rate upon establishment of infection, can provide the position of a QTL associated with resistance to that disease.

The markers identified herein can be used is various aspects of the presently disclosed subject matter as set forth hereinbelow. Aspects of the presently disclosed subject matter are not to be limited to the use of the markers identified herein, however. It is stressed that the aspects can also make use of markers not explicitly disclosed herein or even yet to be identified. Other than the genetic unit "gene", on which the phenotypic expression depends on a large number of factors that cannot be predicted, the genetic unit "QTL" denotes a region on the genome that is directly related to a phenotypic quantifiable trait.

The five QTLs identified herein are located on five different chromosomes or linkage groups and their locations can be characterized by a number of otherwise arbitrary markers. In the present investigations, microsatellite markers (e.g., SSRs), were used, although restriction fragment length polymorphism (RFLP) markers, amplified fragment length polymorphism (AFLP) markers, single nucleotide polymorphisms (SNPs), insertion mutation markers, sequence-characterized amplified region (SCAR) markers, cleaved amplified polymorphic sequence (CAPS) markers or isozyme markers or combinations of these markers might also have been used, and indeed can be used.

In general, a QTL can span a region of several million bases. Therefore, providing the complete sequence information for the QTL is practically unfeasible but also unnecessary, as the way in which the QTL is first detected—through the observed correlation between the presence of a string of contiguous genomic markers and the presence of a particular phenotypic trait—allows one to trace among a population of offspring plants those plants that have the genetic potential for exhibiting a particular phenotypic trait. By providing a non-limiting list of markers, the presently disclosed subject matter thus provides for the effective use of the presently disclosed QTLs in a breeding program.

In some embodiments, a marker is specific for a particular line of descent. Thus, a specific trait can be associated with a particular marker. The markers as disclosed herein not only indicate the location of the QTL, they also correlate with the presence of the specific phenotypic trait in a plant. It is noted that the contiguous genomic markers that indicate the location of the QTL on the genome are in principal arbitrary or non-limiting. In general, the location of a QTL is indicated by a contiguous string of markers that exhibit statistical correlation to the phenotypic trait. Once a marker is found outside that string (i.e., one that has a LOD-score below a certain threshold, indicating that the marker is so remote that recombination in the region between that marker and the QTL occurs so frequently that the presence of the marker does not correlate in a statistically significant manner to the presence of the phenotype) the boundaries of the QTL can be considered set. Thus, it is also possible to indicate the location of the QTL by other markers located within that specified region.

It is further noted that the contiguous genomic markers can also be used to indicate the presence of the QTL (and thus of the phenotype) in an individual plant, which in some embodiments means that they can be used in marker-assisted selection (MAS) procedures. In principle, the number of potentially useful markers is limited but can be very large, and one of ordinary skill in the art can easily identify markers in addition to those specifically disclosed in the present application. Any marker that is linked to the QTL (e.g., falling within the physically boundaries of the genomic region spanned by the markers having established LOD scores above a certain threshold thereby indicating that no or very little recombination between the marker and the QTL occurs in crosses, as well as any marker in linkage disequilibrium to the QTL, as well as markers that represent the actual causal mutations within the QTL) can be used in MAS procedures. This means that the markers identified in the application as associated to the QTLs, such as the SSR markers 3.1, 3.2, 6.1, 6.2, 7.1, 7.2, 9.1, 9.2, 9.3, 10.1, and 10.2 QTL1-QTL5, are mere examples of markers suitable for use in MAS procedures. Moreover, when the QTL, or the specific trait-conferring part thereof, is introgressed into another genetic background (i.e., into the genome of another melon or another plant species), then some markers might no longer be found in the offspring although the trait is present therein, indicating that such markers are outside the genomic region that represents the specific trait-conferring part of the QTL in the original parent line only and that the new genetic background has a different genomic organization. Such markers of which the absence indicates the successful introduction of the genetic element in the offspring are called "trans markers" and can be equally suitable in MAS procedures under the presently disclosed subject matter.

Upon the identification of a QTL, the QTL effect (e.g., the resistance) can for instance be confirmed by assessing resistance in progeny segregating for the QTLs under investigation. The assessment of the resistance can suitably be performed by using a resistance bioassay as known in the art for FOM race 1,2. For example, (field) trials under natural and/or artificial infection conditions can be conducted to assess the resistance of hybrid and/or inbred melons to FOM race 1,2, or if desired, any other FOM race.

The markers provided by the presently disclosed subject matter can be used for detecting the presence of one or more FOM race 1,2 resistance alleles at QTLs of the presently disclosed subject matter in a suspected FOM-resistant melon plant, and can therefore be used in methods involving marker-assisted breeding and selection of FOM (e.g., FOM race 1,2) resistant melon plants. In some embodiments, detecting the presence of a QTL of the presently disclosed subject matter is performed with at least one of the markers for a QTL as defined herein. The presently disclosed subject matter therefore relates in another aspect to a method for detecting the presence of a QTL for FOM race 1,2 resistance, comprising detecting the presence of a nucleic acid sequence of the QTL in a suspected FOM race 1,2-resistant melon plant, which presence can be detected by the use of the disclosed markers.

The nucleotide sequence of a QTL of the presently disclosed subject matter can for instance be resolved by determining the nucleotide sequence of one or more markers associated with the QTL and designing internal primers for the marker sequences that can then be used to further determine the sequence of the QTL outside of the marker sequences. For instance, the nucleotide sequence of the SSR markers disclosed herein can be obtained by isolating the markers from the electrophoresis gel used in the determination of the presence of the markers in the genome of a subject plant, and determining the nucleotide sequence of the markers by, for example, dideoxy chain termination sequencing methods, which are well known in the art.

In embodiments of such methods for detecting the presence of a QTL in a suspected FOM race 1,2-resistant melon plant, the method can also comprise providing a oligonucleotide or polynucleotide capable of hybridizing under stringent hybridization conditions to a nucleic acid sequence of a marker linked to the QTL, in some embodiments selected from the markers disclosed herein, contacting the oligonucleotide or polynucleotide with digested genomic nucleic acid of a suspected FOM race 1,2-resistant melon plant, and determining the presence of specific hybridization of the oligonucleotide or polynucleotide to the digested genomic nucleic acid.

In some embodiments, the method is performed on a nucleic acid sample obtained from the suspected FOM race 1,2-resistant melon plant, although in situ hybridization methods can also be employed. Alternatively, one of ordinary skill in the art can, once the nucleotide sequence of the QTL has been determined, design specific hybridization probes or oligonucleotides capable of hybridizing under stringent hybridization conditions to the nucleic acid sequence of the QTL and can use such hybridization probes in methods for detecting the presence of a QTL disclosed herein in a suspected FOM race 1,2-resistant melon plant.

IV. PRODUCTION OF FOM RACE 1,2-RESISTANT MELON PLANTS BY TRANSGENIC METHODS

According to another aspect of the presently disclosed subject matter, a nucleic acid (in some embodiments a DNA) sequence comprising, one or more of QTL1-QTL5 or resistance-conferring parts thereof, can be used for the production of a resistant melon plant of the presently disclosed subject matter. In this aspect, the presently disclosed subject matter provides for the use of QTLs as defined herein or resistance-conferring parts thereof, for producing a resistant melon plant, which use involves the introduction of a nucleic acid sequence comprising the QTL into a suitable recipient plant. As stated, the nucleic acid sequence can be derived from a suitable FOM race 1,2-resistant donor plant. A suitable source for the FOM race 1,2 resistance locus identified herein as any of QTL1-QTL5 is Rupia, originating from Japan (Mikado Seed Growers Co. Ltd., Chiba City, Japan).

A number of melon cultivars that have varying degrees of resistance to FOM race 1,2 are commercially available. Melon plants that have demonstrated some resistance to FOM race 1,2 resistant include, but are not limited to Isabelle (INRA); Manta, Tolosa, Targa, Tadeo, and Flavio (Clause Tezier SA, Valence, France); Sting (Nunhems, Netherlands BV, Haelen, The Netherlands); and Raffal, Zeffir, Helfi, Neffiac, and Fidji (Gautier Graines SA, Eyragues, France).

The source of the resistance loci described herein is the *Cucumis melo* L. cv. Rupia F1 cultivar (Mikado Seed Growers Co. Ltd.), which was originally generated by crossing an orange-fleshed Japanese *Cucumis melo* with an unknown resistant melon that was green-fleshed. However, the Rupia F1 is thus heterozygous for flesh color, which is undesirable for the purposes of commercial melon production.

Additionally, it was determined through the experiments disclosed herein that at least one of the FOM race 1,2 resistance alleles present within the genome of Rupia was very tightly linked to a green flesh color allele within QTL4 present on chromosome 9. For various reasons, it is desirable to produce a *Cucumis melo* variety that is (a) homozygous for orange flesh (i.e., lacks green flesh alleles); and (b) Includes the FOM race 1,2 resistance alleles present on chromosome 9. In order to accomplish this, the chromosome 9 green flesh allele(s) and FOM race 1,2 resistance allele(s) had to be segregated from each other in a progeny plant derived from breeding Rupia (or a descendent thereof) to another *Cucumis melo* line (e.g., an orange flesh color line). This has now been accomplished, as disclosed herein.

Once identified in a suitable donor plant, the nucleic acid sequence that comprises a QTL for FOM race 1,2-resistance, or a resistance-conferring part thereof, can be transferred to a suitable recipient plant by any method available. For instance, the nucleic acid sequence can be transferred by crossing a FOM race 1,2-resistant donor plant with a susceptible recipient plant (i.e., by introgression), by transformation, by protoplast fusion, by a doubled haploid technique, by embryo rescue, or by any other nucleic acid transfer system, optionally followed by selection of offspring plants comprising one or more of the presently disclosed QTLs and exhibiting resistance. For transgenic methods of transfer, a nucleic, acid sequence comprising a QTL for FOM race 1,2-resistance, or a resistance-conferring part thereof, can be isolated from the donor plant using methods known in the art, and the thus isolated nucleic acid sequence can be transferred to the recipient plant by transgenic methods, for instance by means of a vector, in a gamete, or in any other suitable transfer element, such as a ballistic particle coated with the nucleic acid sequence.

Plant transformation generally involves the construction of an expression vector that will function in plant cells. In the presently disclosed subject matter, such a vector comprises a nucleic acid sequence that comprises a QTL for FOM race 1,2 resistance, or a resistance-conferring part thereof, which vector can comprise a FOM race 1,2-conferring gene that is under control of or operatively linked to a regulatory element, such as a promoter. The expression vector can contain one or more such operably linked gene/regulatory element combinations, provided that at least one of the genes contained in the combinations encodes FOM race 1,2-resistance. The vector(s) can be in the form of a plasmid, and can be used, alone or in combination with other plasmids, to provide transgenic plants that are resistant to FOM race 1,2, using transformation methods known in the art, such as the *Agrobacterium* transformation system.

Expression vectors can include at least one marker gene, operably linked to a regulatory element (such as a promoter) that allows transformed cells containing the marker to be either recovered by negative selection (by inhibiting the growth of cells that do not contain the selectable marker gene), or by positive selection (by screening for the product encoded by the marker gene). Many commonly used selectable marker genes for plant transformation are known in the art, and include, for example, genes that code for enzymes that metabolically detoxify a selective chemical agent that can be an antibiotic or a herbicide, or genes that encode an altered target which is insensitive to the inhibitor. Several positive selection methods are known in the art, such as mannose selection. Alternatively, marker-less transformation can be used to obtain plants without the aforementioned marker genes, the techniques for which are also known in the art.

One method for introducing an expression vector into a plant is based on the natural transformation system of *Agrobacterium* (see e.g., Horsch et al., 1985). *A. tumefaciens* and *A. rhizogenes* are plant pathogenic soil bacteria that genetically transform plant cells. The Ti and Ri plasmids of *A. tumefaciens* and *A. rhizogenes*, respectively, carry genes responsible for genetic transformation of the plant (see e.g., Kado, 1991). Methods of introducing expression vectors into plant tissue include the direct infection or co-cultivation of plant cells with *Agrobacterium tumefaciens* (Horsch et al., 1985). Descriptions of *Agrobacterium* vectors systems and methods for *Agrobacterium*-mediated gene transfer provided by Gruber & Crosby, 1993, Moloney et al., 1989, and U.S. Pat. No. 5,591,616. General descriptions of plant expression vectors and reporter genes and transformation protocols and descriptions of *Agrobacterium* vector systems and methods for *Agrobacterium*-mediated gene transfer can be found in Gruber & Crosby, 1993. General methods of culturing plant tissues are provided for example by Miki et al., 1993 and by Phillips et al., 1988. A reference handbook for molecular cloning techniques and suitable expression vectors is Sambrook & Russell, 2001.

Another method for introducing an expression vector into a plant is based on microprojectile-mediated transformation wherein DNA is carried on the surface of microprojectiles. The expression vector is introduced into plant tissues with a biolistic device that accelerates the microprojectiles to speeds of 300 to 600 m/s which is sufficient to penetrate plant cell walls and membranes (see e.g., Sanford et al., 1987; Klein et al., 1988; Sanford, 1988; Sanford, 1990; Klein et al., 1992;

Sanford et al., 1993). Another method for introducing DNA to plants is via the sonication of target cells (see Zhang et al., 1991). Alternatively, liposome or spheroplast fusion can be used to introduce expression vectors into plants (see e.g., Deshayes et al, 1985 and Christou et al., 1987). Direct uptake of DNA into protoplasts using $CaCl_2$ precipitation, polyvinyl alcohol, or poly-L-ornithine has also been reported (see e.g., Hain et al. 1985 and Draper et al., 1982). Electroporation of protoplasts and whole cells and tissues has also been described (D'Halluin et al., 1992 and Laursen et al., 1994).

Other well known techniques such as the use of BACs, wherein parts of the melon genome are introduced into bacterial artificial chromosomes (BACs), i.e., vectors used to clone DNA fragments (100- to 300-kb insert size; average, 150 kb) in *Escherichia coli* cells, based on naturally occurring F-factor plasmid found in the bacterium *E. coli*. (Zhao & Stodolsky, 2004) can be employed for example in combination with the BIBAC system (Hamilton, 1997) to produce transgenic plants.

Following transformation of melon target tissues, expression of the above described selectable marker genes allows for preferential selection of transformed cells, tissues and/or plants, using standard regeneration and selection methods.

V. PRODUCTION OF FOM RACE 1,2-RESISTANT MELON PLANTS BY NON-TRANSGENIC METHODS

In some embodiments for producing an FOM race 1,2-resistant melon plant, protoplast fusion can be used for the transfer of nucleic acids from a donor plant to a recipient plant. Protoplast fusion is an induced or spontaneous union, such as a somatic hybridization, between two or more protoplasts (cells of which the cell walls are removed by enzymatic treatment) to produce a single bi- or multi-nucleate cell. The fused cell, which can even be obtained with plant species that cannot be interbred in nature, is tissue cultured into a hybrid plant exhibiting the desirable combination of traits. More specifically, a first protoplast can be obtained from a melon plant or other plant line that exhibits resistance to infection by FOM race 1,2. A second protoplast can be obtained from a second melon or other plant variety, preferably a melon line that comprises commercially valuable characteristics, such as, but not limited to disease resistance, insect resistance, valuable fruit characteristics, and the like. The protoplasts are then fused using traditional protoplast fusion procedures, which are known in the art.

Alternatively, embryo rescue can be employed in the transfer of a nucleic acid comprising one or more QTLs as described herein from a donor plant to a recipient plant. Embryo rescue can be used as a procedure to isolate embryo's from crosses wherein plants fail to produce viable seed. In this process, the fertilized ovary or immature seed of a plant is tissue cultured to create new plants (Pierik, 1999).

The presently disclosed subject matter also relates to methods for producing an FOM race 1,2-resistant melon plant comprising performing a method for detecting the presence of a quantitative resistance locus (QTL) associated with resistance to FOM race 1,2 in a donor melon plant according to the presently disclosed subject matter as described above, and transferring a nucleic acid sequence comprising at least one QTL thus detected, or a FOM race 1,2 resistance-conferring part thereof, from the donor plant to a FOM race 1,2-susceptible recipient melon plant. The transfer of the nucleic acid sequence can be performed by any of the methods previously described herein.

An exemplary embodiment of such a method comprises the transfer by introgression of the nucleic acid sequence from a FOM race 1,2-resistant donor melon plant into a FOM race 1,2-susceptible recipient melon plant by crossing the plants. This transfer can thus suitably be accomplished by using traditional breeding techniques. QTLs are introgressed in some embodiments into commercial melon varieties using marker-assisted selection (MAS) or marker-assisted breeding (MAB). MAS and MAB involves the use of one or more of the molecular markers for the identification and selection of those offspring plants that contain one or more of the genes that encode for the desired trait. In the context of the presently disclosed, subject matter, such identification and selection is based on selection of QTLs of the presently disclosed subject matter or markers associated therewith. MAS can also be used to develop near-isogenic lines (NIL) harboring the QTL of interest, allowing a more detailed study of each QTL effect and is also an effective method for development of backcross inbred line (BIL) populations (see e.g., Nesbitt & Tanksley, 2001; van Berloo et al., 200.1). Melon plants developed according to these embodiments can advantageously derive a majority of their traits from the recipient plant, and derive FOM race 1,2 resistance from the donor plant.

As discussed hereinabove, traditional breeding techniques can be used to introgress a nucleic acid sequence encoding for FOM race 1,2 resistance into a FOM race 1,2-susceptible recipient melon plant. In some embodiments, a donor melon plant that exhibits resistance to FOM race 1,2 and comprising a nucleic acid sequence encoding for FOM race 1,2 resistance is crossed with a FOM race 1,2-susceptible recipient melon plant that in some embodiments exhibits commercially desirable characteristics, such as, but not limited to, disease resistance, insect resistance, valuable fruit characteristics, and the like The resulting plant population (representing the F1 hybrids) is then self-pollinated and set seeds (F2 seeds). The F2 plants grown from the F2 seeds are then screened for resistance to FOM race 1,2. The population can be screened in a number of different ways.

First, the population can be screened using a traditional disease screen. Such disease screens are known in the art. In some embodiments, a quantitative bioassay is used. Second, marker-assisted selection can be performed using one or more of the herein-described molecular markers to identify those progeny that comprise a nucleic acid sequence encoding for FOM race 1,2. Other methods, referred to hereinabove by methods for detecting the presence of a QTL, can be used. Also, marker-assisted selection can be used to confirm the results obtained from the quantitative bioassays, and therefore, several methods can also be used in combination.

Inbred FOM race 1,2-resistant melon plant lines can be developed using the techniques of recurrent selection and backcrossing, selfing, and/or dihaploids, or any other technique used to make parental lines. In a method of recurrent selection and backcrossing, FOM race 1,2 resistance can be introgressed into a target recipient plant (the recurrent parent) by crossing the recurrent parent with a first donor plant, which differs from the recurrent parent and is referred to herein as the "non-recurrent parent". The recurrent parent is a plant that is non-resistant or has a low level of resistance to FOM race 1,2 and possesses commercially desirable characteristics, such as, but not limited to (additional) disease resistance, insect resistance, valuable fruit characteristics, and the like. In some embodiments, the non-recurrent parent exhibits FOM race 1,2 resistance and comprises a nucleic acid sequence that encodes for FOM race 1,2 resistance. The non-recurrent parent can be any plant variety or inbred line that is cross-fertile with the recurrent parent.

The progeny resulting from a cross between the recurrent parent and non-recurrent parent are backcrossed to the recurrent parent. The resulting plant population is then screened for the desired characteristics, which screening can occur in a number of different ways. For instance, the population can be screened using phenotypic pathology screens or quantitative bioassays as known in the art. Alternatively, instead of using bioassays, marker-assisted selection (MAS) can be performed using one or more of the hereinbefore described molecular markers, hybridization probes, or polynucleotides to identify those progeny that comprise a nucleic acid sequence encoding for FOM race 1,2 resistance. Also, MAS can be used to confirm the results obtained from the quantitative bioassays. In some embodiments, the markers defined herein are suitable to select proper offspring plants by genotypic screening.

Following screening, the F1 hybrid plants that exhibit a FOM race 1,2-resistant phenotype or, in some embodiments, genotype and thus comprise the requisite nucleic acid sequence encoding for FOM race 1,2 resistance, are then selected and backcrossed to the recurrent parent for a number of generations in order to allow for the melon plant to become increasingly inbred. This process can be performed for two, three, four, five, six, seven, eight, or more generations. In principle, the progeny resulting from the process of crossing the recurrent parent with the FOM race 1,2-resistant non-recurrent parent are heterozygous for one or more genes that encode FOM race 1,2 resistance.

In general, a method of introducing a desired trait into a hybrid melon variety can comprise:

(a) crossing an inbred melon parent with another melon plant that comprises one or more desired traits, to produce F1 progeny plants, wherein the desired trait is FOM race 1,2 resistance;

(b) selecting the F1 progeny plants that have the desired trait to produce selected F1 progeny plants, in some embodiments using molecular markers as defined herein;

(c) backcrossing the selected progeny plants with the inbred melon parent plant to produce backcross progeny plants;

(d) selecting for backcross progeny plants that have the desired trait and morphological and physiological characteristics of the inbred melon parent plant, wherein the selection comprises the isolation of genomic DNA and testing the DNA for the presence of at least one molecular marker for QTL1, QTL2, QTL3, QTL4, and/or QTL5, in some embodiments as described herein;

(e) repeating steps (c) and (d) two or more times in succession to produce selected third or higher backcross progeny plants;

(f) optionally selfing selected backcross progeny in order to identify homozygous plants; and (g) crossing at least one of the backcross progeny or selfed plants with another inbred melon parent plant to generate a hybrid melon variety with the desired trait and all of the morphological and physiological characteristics of hybrid melon variety when grown in the same environmental conditions.

As indicated, the last backcross generation can be selfed in order to provide for homozygous pure breeding (inbred) progeny for FOM race 1,2 resistance. Thus, the result of recurrent selection, backcrossing, and selfing is the production of lines that are genetically homogenous for the genes associated with FOM race 1,2 resistance, and in some embodiments as well as for other genes associated with traits of commercial interest.

VI. FOM RACE 1,2-RESISTANT MELON PLANTS AND SEEDS

The goal of plant breeding is to combine in a single variety or hybrid various desirable traits. For commercial crops, these traits can include resistance to diseases and insects, tolerance to heat and drought, reducing the time to crop maturity, greater yield, and better agronomic quality. Uniformity of plant characteristics such as germination and stand establishment, growth rate, maturity, and plant height can also be of importance.

Commercial crops are bred through techniques that take advantage of the plant's method of pollination. A plant is self-pollinated if pollen from one flower is transferred to the same or another flower of the same plant. A plant is sib pollinated when individuals within the same family or line are used for pollination. A plant is cross-pollinated if the pollen comes from a flower on a different plant from a different family or line.

Plants that have been self-pollinated and selected for type for many generations become homozygous at almost all gene loci and produce a uniform population of true breeding progeny. A cross between two different homozygous lines produces a uniform population of hybrid plants that may be heterozygous for many gene loci. A cross of two plants each heterozygous at a number of gene loci will produce a population of heterogeneous plants that differ genetically and will not be uniform.

The development of a hybrid melon variety in a melon plant breeding program can, in some embodiments, involve three steps: (1) the selection of plants from various germplasm pools for initial breeding crosses; (2) the selling of the selected plants from the breeding crosses for several generations to produce a series of inbred lines, which, individually breed true and are highly uniform; and (3) crossing a selected inbred line with an unrelated inbred line to produce the hybrid progeny (F1). After a sufficient amount of inbreeding successive filial generations will merely serve to increase seed of the developed inbred. In some embodiments, an inbred line comprises homozygous alleles at about 95% or more of its loci.

An important consequence of the homozygosity and homogeneity of the inbred lines is that the hybrid created by crossing a defined pair of inbreds will always be the same. Once the inbreds that create a superior hybrid have been identified, a continual supply of the hybrid seed can be produced using these inbred parents and the hybrid melon plants can then be generated from this hybrid seed supply.

A FOM race 1,2-resistant melon plant, or a part thereof, obtainable by a method of the presently disclosed subject matter is an aspect of the presently disclosed subject matter.

Another aspect of the presently disclosed subject matter relates to a FOM race 1,2-resistant melon plant, or part thereof, comprising the QTLs in any configuration as described in detail above wherein at least one of the QTLs is not in its natural genetic background. The FOM race 1,2-resistant melon plants of the presently disclosed subject matter can be of any genetic type such as inbred, hybrid, haploid, dihaploid, or transgenic. Further, the plants of the presently disclosed subject matter can be heterozygous or homozygous for the resistance traits (in some embodiments, homozygous). Although the QTLs of the presently disclosed subject matter, as well as resistance-conferring parts thereof, can be transferred to any plant in order to provide for a FOM race 1,2-resistant plant, the methods and plants of the presently disclosed subject matter are in some embodiments related to plants of the species *Cucumis melo*.

The FOM race 1,2-resistant inbred melon lines described herein can be used in additional crossings to create FOM race 1,2-resistant hybrid plants. For example, a first FOM race 1,2-resistant inbred melon plant of the presently disclosed subject matter can be crossed with a second inbred melon plant possessing commercially desirable traits such as, but not limited to, disease resistance, insect resistance, desirable fruit characteristics, and the like. In some embodiments, this second inbred melon line is FOM race 1,2-resistant. In some embodiments, this line is homozygous for one or more of QTL1-QTL5, in order for this recessive trait to be expressed in the hybrid offspring plants.

Another aspect of the presently disclosed subject matter relates to a method of producing seeds that can be grown into FOM race 1,2-resistant melon plants. In some embodiments, the method comprises providing a FOM race 1,2-resistant melon plant of the presently disclosed subject matter, crossing the FOM race 1,2-resistant plant with another melon plant, and collecting seeds resulting from the cross, which when planted, produce FOM race 1,2-resistant melon plants.

In some embodiments, the method comprises providing a FOM race 1,2-resistant melon plant of the presently disclosed subject matter, crossing the FOM race 1,2-resistant plant with a melon plant, collecting seeds resulting from the cross, regenerating the seeds into plants, selecting FOM race 1,2-resistant plants by any of the methods described herein, self-pollinating the selected plants for a sufficient number of generations to obtain plants that are fixed for an allele that confers FOM race 1,2-resistance in the plants, backcrossing the plants thus produced with melon plants having desirable phenotypic traits for a sufficient number of generations to obtain melon plants that are FOM race 1,2-resistant and have desirable phenotypic traits, and collecting the seeds produced from the plants resulting from the last backcross, which when planted, produce melon plants which are FOM race 1,2-resistant.

EXAMPLES

The following Examples provide illustrative embodiments. In light of the present disclosure and the general level of skill in the art, those of skill will appreciate that the following Examples are intended to be exemplary only and that numerous changes, modifications, and alterations can be employed without departing from the scope of the presently claimed subject matter.

Example 1

Initial Plant Materials

Rupia F1 plants were obtained from Mikado Seed Growers Co. Ltd. and self-pollinated to produce an F2, several individuals of which were self-pollinated to produce 18 F3 lines. Plants of these F3 lines (referred to herein as "MFR0029520") were crossed with an F6 Charentais line (referred to herein as "MFR0017377"), a line selected from the Lunastar line (Nunhems Netherlands BV) to produce line referred to herein as "MFR0037489", which was then backcrossed with the F6 Charentais line MFR0017377 to obtain single backcross (BC1) line referred to herein as "MFR0039432". Double haploidization was performed on a plant of BC1 line MFR0039432, and 29 double haploid lines were obtained. One such double haploid, referred to herein as "03MFR001795", was selected for good resistance to *F. oxysporum* f.sp. *melonis* race 1,2 in climatic chambers according to the phenotypic evaluation described in the EXAMPLE 3 below. This male plant had green flesh color. The 03MFR001795 double haploid line was crossed with a second Charentais F6 line MFR0040308 to produce a hybrid referred to herein as "02MFR005456". This hybrid was selfed to produce F2 seed.

Example 2

Recombinant Inbred Lines Development Using the Single Seed Descent (SSD) Method

200 F2 plants from the selfing of 02MFR005456 were self-pollinated and 199 F3 lines were obtained. All 199 F3 lines were sown, and one plant per F3 was transplanted and self-pollinated to generate 196 F4 lines. These 196 F4 lines were sown, and one plant per F4 was transplanted and self-pollinated to generate 194 F5 lines. These 194 F5 lines were sown, and one plant per F5 was transplanted and self-pollinated to generate 183 F6 lines. These 183 F6 lines were sown, and one plant per F6 was transplanted and self-pollinated to generate 177 F7 lines.

Leaf tissue from each F6 plant was collected and used for DNA extraction sand genotyping.

F7 seeds that were produced by each F6 plant were harvested, and all F7 seeds harvested were kept separated by F6 plant of origin, thereby constituting 177 F7 families. The 177 F7 families were evaluated for *F. oxysporum* f.sp. *melonis* race 1,2 resistance in the sand test.

Example 3

Phenotypic Evaluation

Fungal Strain.

A yellowing isolate of *Fusarium oxysporum* f.sp. *melonis* race 1,2 was used for the phenotypic evaluations of the RIL population and also of lines and hybrids from breeding programs. The strain was maintained on Petri dishes with agar medium S under controlled temperature at 20° C. Medium S contains 1 g/l $Ca(NO_3)_2$, 0.25 g/l $KNO_3$, 0.25 g/l $MgSO_4$, 0.125 g/l $KH_2PO_4$, 0.125 g/l $K_2HPO_4$, 0.05 g/l citric acid, 5 g/l malt, and 50 g/l sucrose. For solid medium, 25 g of agar was added per liter of medium S, and the material was autoclaved to sterility, cooled, and poured onto Petri dishes.

A monthly subculture was made from a small piece of agar containing mycelium into a new sterile Petri dish. Active cultures were obtained by placing a small piece of agar containing mycelium in a flask containing 400 ml of medium S and incubating on a rotary shaker at 130 rpm for 3 days at 21° C.

RIL Disease Evaluation.

Among the 177 RILs, 154 lines and controls were evaluated for resistance to *F. oxysporum* f.sp. melons race 1,2 after artificial inoculation. Three independents experiments were carried out. In each experiment, 10 plants of each RIL were evaluated in a complete randomized design with 3 blocks.

Seeds were sown in trays with adapted compost for sowing. Trays were incubated in climatic chambers with a photoperiod of 15 h/9 h (day/night). The temperature during the day was 24° C.±2° C. with a luminosity of 10,000 lux, and during the night the temperature was 18° C.±2° C.

The inoculation was carried out after 7 days of growth. Seedlings were removed from the compost and roots were washed with water before being incubated for 10 minutes in a solution containing $1 \times 10^6$ spores/ml of a yellowing strain of *F. oxysporum* f.sp. *melonis* race 1,2. Thereafter, seedlings were transplanted in sandy trays with 5 plants per row. Each tray included appropriate controls. Trays were incubated in a climatic chamber with a 12 h/12 h light/dark cycle at a temperature of 22° C./18° C.±2° C. During the light cycle the luminosity was 5000 lux. Trays were watered each day during the first weeks, and then a nutritive solution was added every other watering until the end of the evaluation. (Liquoplant Bleu from Plantin, Courthezon, France; with the following NPK composition: 2.5 (whole nitrogen)–5 ($P_2O_5$)–2.5 ($K_2O$)–0.75 (MgO)+oligo-elements. The solution is diluted to obtain an electro-conductivity of 2 and a pH of 6.5).

The first symptoms (i.e., yellowing on cotyledons) appeared after day 7 post-inoculation. After days 15, 20, and 25 post-inoculation, the evaluation of symptoms was assessed on infected leaves using a semi-quantitative rating scale from 1 to 5 as follows:
1=no symptoms;
2=yellowing of the cotyledons or the first leaf;
3=yellowing of two leaves;
4=yellowing of three or more leaves;
5=death of plant.

The susceptible plants showed a yellowing on cotyledons after 7 days, stop growing, and died within a few days. The intermediate resistant plants showed slowed growth and symptoms appeared on new leaves. The resistant plants did not show any symptoms on leaves and grew at a normal rate.

25 days post-inoculation, all plants were scored on the semi-quantitative rating scale (1-5) above. The disease scores were calculated for each RIL using a mean by line, by block, and by experiment. For each RIL, a mean disease score of each plant was recorded.

Lines and Hybrids Evaluation in a Breeding Program.

Lines were evaluated under similar conditions as indicated for the RIL population; but the trial design was simplified by testing 20 plants per line. the evaluation of symptoms was assessed on infected leaves using, the same semi-quantitative 1-9 rating scale defined below for hybrids evaluation Hybrid evaluation was performed on 3 replicates of 8 plants per hybrid. Seeds were sown in trays with adapted compost for sowing. Trays were incubated in climatic chambers with a photoperiod of 15 h/9 h (day/night). The temperature during the day was 24° C.±2° C. with a luminosity of 10,000 lux, and during the night the temperature was 18° C.±2° C.

Six (6) days after sowing, seedlings were transplanted into trays containing 96 conical pots each with a diameter of 6 cm. Trays were incubated in a climatic chamber (12 h/12 h day/night) at 22° C./18° C.±2° C. During the day cycle, the luminosity was 5000 lux. Trays were watered each day during the first weeks then a nutritive solution was added as set forth hereinabove.

One week later (i.e., at day 15 post-sowing), when the first true leaf measured a few cm in length, plants were inoculated by soaking the tray into a spore solution containing $1 \times 10^5$ spores/ml for 10 minutes.

The first symptoms (i.e., a yellowing on cotyledons) appeared after day 10 post-inoculation. After days 15, 20, and 25 post-inoculation, the evaluation of symptoms was assessed on infected leaves using a semi-quantitative rating scale from 1 to 3 as follows:
1=Resistant (no symptoms)
2=Intermediate Resistance (yellowing of the cotyledons or the first leaf)
3=Susceptible (yellowing of two or more leaves)

The disease score at the third scoring date (day 25 post-inoculation) was assessed for each plant of the hybrid. To stretch the scale and to compare hybrids, a score of from 1 to 9 was calculated for each hybrid using the following calculation:

Store=$((X \times 9)+(Y \times 5)+(Z \times 1))/(X+Y+Z)$, wherein:
X=number of plants for an hybrid with a score equal to 3;
Y=number of plants for an hybrid with a score equal to 2; and
Z=number of plants for an hybrid with a score equal to 1.

Example 4

Genotyping and QTL Mapping

DNA was extracted from F6 leaves and DNA samples were genotyped using 82 polymorphic SSRs. Several hundred SSRs covering the entire melon genome had been previously run on the two parents of this segregating population, MC7752, in order to identify the polymorphic ones. A molecular marker map was constructed using MapMaker (Lander et al., 1987) and JoinMap (Stam, 1993) software. Joint-analysis of genotypic and phenotypic data was performed using the software QTL Cartographer and PLABQTL (Utz & Melchinger, 1996). Five QTLs were identified for *Fusarium oxysporum* f.sp. *melonis* race 1,2 resistance on chromosomes 3, 6, 7, 9, and 10. These QTLs are characterized by their position on the genetic map and their additive and dominant effects. Positions were defined as genetic distances between the most likely position of the QTLs (usually the position of the peak LOD score value) and linked marker loci (in centiMorgans). Additive effects were defined as deviations from the mean and were expressed in the same units as the trait they refer to (i.e., 1 to 5 scale, where 1 is fully resistant and 5 is fully susceptible family). Additive values defined which of the two parental lines carried the favorable allele at the QTL. In this case, positive additive values identified for all five QTLs meant that the 03MFR001795 parent carried the favorable alleles for these QTLs.

The position of the five QTLs identified relative to neighboring markers, along with their effects and favorable alleles, are presented in Table 1. These QTLs were thus the selection targets for the development of new *Fusarium oxysporum* f.sp. *melonis* race 1,2 resistant lines.

TABLE 1

QTLs for *F. oxysporum* f.sp *melonis*
Race 1, 2 Resistance and Linked Markers

| QTL # | Chrom | QTL Begin (cM)* | QTL Position (cM)* | QTL End (cM)* | Effect (Add Value) | Linked Markers** |
|---|---|---|---|---|---|---|
| 1 | 3 | 81.1 | 90.2 | 94.4 | 0.34 | 3.1, 3.2 |
| 2 | 6 | 6.6 | 13.6 | 28.8 | 0.32 | 6.1, 6.2 |
| 3 | 7 | 1.3 | 9.3 | 19.1 | 0.23 | 7.1, 7.2 |
| 4 | 9 | 3.2 | 21.1 | 23.7 | 0.54 | 9.1, 9.2, 9.3 |
| 5 | 10 | n.d | ~43 | n.d | 0.22 | 10.1, 10.2 |

*these values are approximate and are based on the mapping population employed herein. One of ordinary skill in the art would recognize that in different mapping populations, the absolute positions might vary, although the placement of the markers on chromosomes relative to each other would not be expected to differ.
n.d.: not determined.
**For QTLs 1, 2, 3, and 5, markers 3.1, 6.1, 7.1, and 10.1 map to the position listed under the heading "QTL Begin" for the corresponding QTL, and markers 3.2, 6.2, 7.2, and 10.2 map to the position listed under the heading "QTL End". With respect to QTL4, markers 9.1, 9.2, and 9.3 map to the positions listed under the headings "QTL Begin", "QTL Position", and "QTL END", respectively.

In Table 1, each QTL has been assigned an arbitrary number 1-5. The following information is presented for each QTL: the chromosome on which it is located, its most likely position on that chromosome (i.e., the position with the highest LOD score), the beginning and end of its confidence interval, its effect (additive value) as characterized by the difference between the effect of the allele from 03MFR001795 and that of the allele from MFR0040308, and markers linked to the QTL (and therefore diagnostic of the allele present at the QTL).

For example, the first QTL for *F. oxysporum* f.sp. *melonis* race 1,2 resistance was located on chromosome 3, with a most likely position at 90.2 cM and with a confidence interval ranging from 80.7 cM to 99.4 cM. The effect of the QTL is 0.34, which means that the allele 03MFR001795 increased resistance by 0.34 compared to the allele from MFR0040308.

Example 5

Determination of Allele Characteristics (Amplified Fragment Size) by PCR

In all identified QTLs, the favorable allele came from 03MFR001795 (deposited with NCIMB Ltd. under the terms of the Budapest Treaty on 27 Apr. 2007 as Accession No. 41478). A PCR assay and/or the sequencing assay set forth in EXAMPLE 6 were employed to screen DNA isolated from plants for the presence of these alleles. This information was used to select individuals during the marker-based selection process, the objective of which is to maximize the number of favorable alleles for *F. oxysporum* f.sp. *melonis* race 1,2 resistance present in one individual.

Three (3) μl of extracted plant DNA to be tested (concentration equals 2 ng/μl) was distributed in to wells of 384-well plates. 3 μl of PCR mix A was also added to the wells. The composition of PCR mix A was 1×PCR buffer containing 1.65 mM $MgCl_2$, each dNTP at 62.5 μM, 0.033 units/μl Invitrogen PLATINUM® Taq polymerase (Invitrogen Corp., Carlsbad, Calif., United States of America), and M13/forward and reverse primers at 412 nM each. The sequences of the primers employed are as follows:

QTL 1 (Chromosome 3):
- 3.1: M13/forward primer GTTTTCCCAGTCACGACGCGTCATAGCG TACTTAGC (SEQ ID NO: 23/SEQ ID NO: 1) and reverse primer ATTTGTTTTGCCATTTCTG (SEQ ID NO: 2). Size of fragment from desired allele: 339 basepairs (bp).
- 3.2: M13/forward primer GTTTTCCCAGTCACGACCCAAATCGA AACAAAAGTC (SEQ ID NO: 23/SEQ ID NO: 3) and reverse primer TGTTAGATTTGTTGCAGGC (SEQ ID NO: 4). Size of fragment from desired allele: 320 bp.

QTL 2 (Chromosome 6):
- 6.1: M13/forward primer GTTTTCCCAGTCACGACACAAAATGGT AATGAAAACTTG (SEQ ID NO: 23/SEQ ID NO: 5) and reverse primer AACAAGAAAGCTACCACGC (SEQ ID NO: 6). Size of fragment from desired allele: 254 bp.
- 6.2: M13/forward primer GTTTTCCCAGTCACGACCCCATGAAAG AAAATGGAG (SEQ ID NO: 23/SEQ ID NO: 7) and reverse primer TTCATCTTCCATCAAACCC (SEQ ID NO: 8). Size of fragment from desired allele: 206 bp.

QTL 3 (Chromosome 7):
- 7.1: M13/forward primer GTTTTCCCAGTCACGACTAGCTTGAACTT CGTCCTG (SEQ ID NO: 23/SEQ ID NO: 9) and reverse primer GAAGCGTACTCCCTATTGC (SEQ ID NO: 10). Size of fragment from desired allele: 238 bp.
- 7.2: M13/forward primer GTTTTCCCAGTCACGACGGCAGTAAAT GACCATGAC (SEQ ID NO: 23/SEQ ID NO: 11) and reverse primer GGTGACGAACAAACTGAAG (SEQ ID NO: 12). Size of fragment from desired allele: 246 bp.

QTL 4 (Chromosome 9):
- 9.1: M13/forward primer GTTTTCCCAGTCACGACTAGCAAAC GACAACTAGGC (SEQ ID NO: 23/SEQ ID NO: 13) and reverse primer GTGGAAAAGAGAGGAAAGG (SEQ ID NO: 14). Size of fragment from desired allele: 346 bp.
- 9.2: M13/forward primer GTTTTCCCAGTCACGACCCCCTCTTAT CTTTTCCTG (SEQ ID NO: 23/SEQ ID NO: 15) and reverse primer CATCAAGAAGTCACGGAAG (SEQ ID NO: 16). Size of fragment from desired allele: 296 bp.
- 9.3: M13/forward primer GTTTTCCCAGTCACGACCCAAAGTAAAAG TGAAGTCC (SEQ ID NO: 23/SEQ ID NO: 17) and reverse primer CTTGAAATGAATTTGAGGTG (SEQ ID NO: 18). Size of fragment from desired allele: 164 bp.

QTL 5 (Chromosome 10):
- 10.1: M13/forward primer GTTTTCCCAGTCACGACTTCTGATCAAC GACGAAG (SEQ ID NO: 23/SEQ ID NO: 19) and reverse primer GAAACAAAAGCCTCCATTG (SEQ ID NO: 20). Size of fragment from desired allele: 263 bp.
- 10.2: M13/forward primer GTTTTCCCAGTCACGACACCCACCATG CATTCTAAC (SEQ ID NO: 23/SEQ ID NO: 21) and reverse primer GAGCCAGTTGGGGTTTTAG (SEQ ID NO: 22). Size of fragment from desired allele: 268 bp.

The PCR amplification was conducted with in a GENEAMP® PCR System 9700 thermocycler (Applied Biosystems, Inc. Foster City, Calif., United States of America) employing the following steps: an initial denaturation of 2 minutes at 94° C.; 40 cycles of 0 seconds at 94° C. followed by 0 seconds at 54° C. and 5 seconds at 72° C. (i.e., 40 cycles of ramping up to 94° C. and down to 54° C., each with no hold time, before a 5 second extension step at 72° C.). Amplified products were separated on agarose gels using high resolution agarose (ULTRAPURE®Agarose 1000 from Invitrogen Corp.) at a concentration of 3% in 1× Tris-borate EDTA (TBE). Electrophoresis was conducted at 400 volts for approximately 1 hour. PCR amplification products were observed after agarose separation using ethidium bromide and viewing under UV light.

Example 6

Determination of Allele Characteristics (Amplified Fragment Size) Using a Sequencer Five (5) μl of DNA at a concentration of 2 ng/μl was distributed into wells of 384-well plates. 5 μl of PCR mix B was also added to the wells. The composition of PCR mix B was 1×PCR buffer containing 1.65 mM $MgCl_2$, each dNTP at 200 μM, 0.033 units/μl Invitrogen PLATINUM® Taq polymerase (Invitrogen Corp.), a M13/forward primer at 800 nM, a reverse primer at 600 nM, and a fluorescent M13 probe at 600 nM. Primer sequences were as shown in EXAMPLE 5. The fluorescent M13 probe included a fluorescent label attached to its 5' end and a nucleotide sequence that specifically hybridized to SEQ ID NO: 23, allowing the fluorescent probe to be employed for detecting the size of the amplified fragments in the sequencer.

PCR amplification was conducted using a GENEAMP® PCR System 9700 thermocycler (Applied Biosystems) and the following steps: an initial denaturation step of 2 minutes at 94° C.; 40 cycles of 15 seconds at 94° C. followed by 45 seconds at 54° C.; and a final extension of 2 minutes at 72° C. PCR amplification products were denatured with formamide for 3 minutes at 96° C. before being separated on an ABI PRISM® 3700 sequencer (Applied Biosystems). Migration in the sequencer took place in capillaries filled with polymer POP-6™ (Applied Biosystems) in 1×TBE. The sizes of the PCR amplification fragments were determined software GENESCAN® and GENOTYPER® software (Applied Biosystems).

Example 7

Introgression of Resistance in Charentais Breeding Material Using Pathology Tests: 06MFR006171 Male Parental Line Example Alleles associated with resistance to *F. oxysporum* f.sp. *melonis* race 1,2 present in Rupia have been introgressed into Charentais breeding material by rescuing resistant plants after sand tests and backcrossing them to Charentais breeding lines. The Charentais melon has orange flesh and is climacteric at maturity.

A Rupia F1 hybrid was crossed in September 2000 to Charentais dihaploid line MFR0038049 to generate Cross RUPIA×MFR0038049. Cross RUPIA×MFR0038049 was placed in a sand test. 36 surviving plants were rescued, grown, and self pollinated in the greenhouse in April 2001. Each plant was backcrossed to dihaploid Charentais line MFR0038049 to obtain 33 BC1 individuals.

These BC1 individuals were tested in a sand test and 2 surviving plants were rescued, grown, and self-pollinated in the greenhouse to obtain 2 F2BC1 lines.

One such F2BC1 line (referred to herein as "MFR0043937") was tested in a sand test and 3 surviving plants were rescued, grown, and self-pollinated in the greenhouse to obtain an F3 line (referred to herein as "02MFR002965") that was heterozygous (orange/green) for flesh color.

F3 line 02MFR002965 (heterozygous for flesh color) was tested in a sand test and 23 surviving plants were rescued, grown, and self-pollinated in the greenhouse. These 23 plants were crossed to an F4 Charentais line (referred to herein as "MFR0043194") to produce a series of progeny plants.

Individuals of these progeny plants were tested in a sand test and 5 surviving plants were rescued, grown, and self-pollinated in the greenhouse. Each plant was crossed with Charentais line 02MFR010858 to generate further progeny.

Individuals of these further progeny were tested in a sand test and 22 surviving plants were rescued, grown, and self-pollinated in the greenhouse. 22 F2 lines were obtained and tested for *Fusarium oxysporum* f.sp. melon's race 1,2 resistance.

These 22 F2 lines were tested in a sand test and surviving plants were rescued, grown, and self-pollinated in the greenhouse. These F2 lines segregated for flesh color. 8 F3 were obtained and tested for *Fusarium oxysporum* f.sp. *melonis* race 1,2 resistance.

An individual F3 line was tested in a sand test and surviving plants were rescued, grown, and self-pollinated in the greenhouse. This F3 line was fixed for orange flesh color. 3 F4 lines were selected and tested for *Fusarium oxysporum* f.sp. *melonis* race 1,2 resistance.

An individual F4 line was tested in a sand test and surviving plants were rescued, grown, and self-pollinated in the greenhouse. 15 F5 lines were obtained. They were tested in a sand test for *Fusarium oxysporum* f.sp. *melonis* race 1,2 resistance.

An individual F5 line was used as a male to cross with susceptible Charentais dihaploid line MFR0044433. The hybrid obtained was referred to as 05MFR013549.

The F5 line was also self-pollinated to generate an F6 line. 05MFR013549 was tested in a phytotron multicell test and showed good resistance to *Fusarium oxysporum* f.sp. *melonis* race 1,2. 05MFR013549 was also evaluated in an open field protected by a small tunnel. The trial field was strongly infected by *Fusarium oxysporum* f.sp. *melonis* race 1,2. The hybrid 05MFR013549 showed an intermediate resistance to *Fusarium oxysporum* f.sp. *melonis* race 1,2.

The F6 line was self pollinated and an F7 line was obtained. The F7 line (06MFR003787) was crossed with line MFR0044433. Hybrid 06MFR006171 was obtained and was tested in a multicell test in a phytotron.

These breeding experiments, along with the results of testing for the presence or absence of representative markers in QTLs 1 and 4, are summarized in Tables 2 and 3.

TABLE 2

Types, Sources, and Flesh Colors of Representative Lines and Hybrids

| MATID | Type | Source | FLC |
|---|---|---|---|
| 1. MFR0040308 | Line | Syngenta | O |
| 2. MFR0038049 | Line | Syngenta | O |
| 3. MFR0025266 | Line | Syngenta | O |
| 4. MFR0044433 | Line | Syngenta | O |
| 5. 03MFR003030 | Line | Syngenta | O |
| 6. RUPIA | Hybrid | Mikado | O |
| 7. 03MFR001795 | Line | Syngenta | G |
| 8. 06MFR003786** | Line | Syngenta | O |
| 9. 06MFR006172 | Hybrid | Syngenta | O |
| 10. 06MFR009993 | Hybrid | Syngenta | O |
| 11. 06MFR003787 | Line | Syngenta | O |
| 12. 06MFR006171 | Hybrid | Syngenta | O |
| 13. 06MFR009975 | Hybrid | Syngenta | O |
| 14. 06MFR004012 | Line | Syngenta | O |
| 15. 06MFR006175 | Hybrid | Syngenta | O |
| 16. 06MFR005919 | Line | Syngenta | O |
| 17. 06MFR009976 | Hybrid | Syngenta | O |
| 18. 06MFR009994 | Hybrid | Syngenta | O |
| 19. FIDJI | Hybrid | Gautier | O |
| 20. MANTA | Hybrid | Clause-Tezier | O |
| 21. AMADORA | Hybrid | Syngenta | O |
| 22. MEHARI | Hybrid | Syngenta | O |

TABLE 3

Presence or Absence of Markers in QTL1 and QTL4

| MATID | Line test* | Hybrid test* | QTL1 Markers 3.1 | 3.2 | QTL4 Markers 9.1 | 9.2 | 9.3 |
|---|---|---|---|---|---|---|---|
| 1. MFR0040308 | 6.6 | — | 0 | 0 | 0 | 0 | 0 |
| 2. MFR0038049 | 7.1 | — | 0 | 0 | 0 | 0 | 0 |
| 3. MFR0025266 | 8.5 | — | 0 | 0 | 0 | 0 | 0 |
| 4. MFR0044433 | 8.7 | — | 0 | 0 | 0 | 0 | 0 |
| 5. 03MFR003030 | 6.8 | — | 0 | 0 | 0 | 0 | 0 |
| 6. RUPIA | 7.3 | 4.0 | 1 | 1 | H | H | H |
| 7. 03MFR001795 | 2.9 | — | 1 | 1 | 1 | 1 | 1 |
| 8. 06MFR003786** | 4.1 | — | 0 | 1 | 0 | 1 | 1 |
| 9. 06MFR006172 | — | 4.0 | 0 | H | 0 | H | H |
| 10. 06MFR009993 | — | 3.2 | 0 | H | 0 | H | H |
| 11. 06MFR003787 | 4.9 | — | 0 | 1 | 0 | 1 | 1 |
| 12. 06MFR006171 | — | 4.2 | 0 | H | 0 | H | H |
| 13. 06MFR009975 | — | 2.2 | 0 | H | 0 | H | H |
| 14. 06MFR004012 | 2.9 | — | 0 | 1 | 0 | 1 | 1 |
| 15. 06MFR006175 | — | 5.2 | 0 | H | 0 | H | H |
| 16. 06MFR005919 | 6.7 | — | 0 | 0 | 0 | 0 | 0 |
| 17. 06MFR009976 | — | 7.7 | 0 | 0 | 0 | 0 | 0 |
| 18. 06MFR009994 | — | 8.2 | 0 | 0 | 0 | 0 | 0 |
| 19. FIDJI | 8.3 | 5.8 | 0 | 0 | 0 | 0 | 0 |
| 20. MANTA | 5.7 | 2.6 | 0 | 0 | 0 | 0 | 0 |
| 21. AMADORA | — | 8.5 | 0 | 0 | 0 | 0 | 0 |
| 22. MEHARI | — | 8.8 | 0 | 0 | 0 | 0 | 0 |

Legend for Tables 2 and 3:
All hybrids and lines were in a Charentais background with the exception of Rupia, which is a Japanese cultivar.

Rows 1-5: FOM race 1,2 susceptible recurrent lines; Row 6: Rupia F1 FOM race 1,2 intermediate resistant from Mikado Seeds; Row 7: FOM race 1,2 resistant donor of RIL mapping population; Rows 8-10: FOM race 1,2 donor line and corresponding hybrids; Rows 11-13: FOM race 1,2 donor line and corresponding hybrid; Rows 14-15: FOM race 1,2 donor line and corresponding hybrid; Rows 16-18: FOM race 1,2 donor line and corresponding hybrids; Rows 19-20: Other commercial hybrids with FOM race 1,2 intermediate resistance levels; Rows 21-22: FOM race 1,2 susceptible hybrid checks.

FLC: flesh color; O: orange; G: green;

*: Resistance to FOM race 1,2 scored on a scale of 1-9 as described herein;

**: this line, 06MFR003786, is homozygous for QTL4 and yet has orange flesh, indicative of a breaking of the linkage between the green flesh color marker(s) present on chromosome 9 and QTL4.

-: not applicable; 0: favored allele absent; 1: favored allele present in homozygous state; H: favored allele present in heterozygous state.

REFERENCES

All references listed below, as well as all references cited in the instant disclosure, including but not limited to all patents, patent applications and publications thereof, scientific journal articles, and database entries (e.g., GENBANK® database entries and all annotations available therein) are incorporated herein by reference in their entireties to the extent that they supplement, explain, provide a background for, or teach methodology, techniques, and/or compositions employed herein.

Altschul et al. (1990) *J Mol Biol* 215:403-10.
Altschul et al. (1997) *Nucleic Acids Res* 25:3389-3402.
Ausubel et al. (eds.) (1999) *Short. Protocols in Molecular Biology* Wiley, New York, N.Y., United States of America.
Christou et al. (1987) *Proc Natl Acad Sci USA* 84:3962-3966.
Deshayes et al. (1985) *EMBO J* 4:2731-2737.
Draper et al. (1982) *Plant Cell Physiol* 23, 451-458.
Glick & Thompson (1993) *Methods in Plant Molecular Biology and Biotechnology*, CRC Press, Boca Raton. Fla., United States of America.
Gruber & Crosby (1993) in Glick & Thompson (eds.) *Methods in Plant Molecular Biology and Biotechnology*, CRC Press, Baton Rouge, La., United States of America, pages 89-119.
Hain at al. (1985) *Mol Gen Genet.* 199:161-168.
Hamilton (1997) *Gene* 200:107-116.
Horsch et al. (1985) *Science* 227:1229-1231.
Kado (1991) *Crit Rev Plant Sci* 10:1-32.
Klein et al. (1988) *Biotechnology* 6:559-563.
Klein at al. (1992) *Bio/Technology* 10:286-291.
Lander et al. (1987) *Genomics* 1:174-181.
Laursen et al, (1994) *Plant Mol Biol* 24:51-61.
Miki et al. (1993). in Glick & Thompson (eds.) *Methods in Plant Molecular Biology & Biotechnology*, CRC Press, Baton Rouge, La., United States of America, pages 67-88.
Moloney et al. (1989) *Plant Cell Rep* 8:238-242.
Nesbitt & Tanksley (2001) *Plant Physiol* 127:575-583.
Paterson (1996) in Paterson (ed.) *Genome Mapping in Plants*. R. G. Landes Company, Georgetown, Tex., United States of America, pages 41-54.
Perchepied et al. (2005) *Theor Appl Genet* 111:65-74.
Perin et al., (2002) *Theor Appl Genet* 104:1017-1034.
Phillips et al. (1988) in Sprague & Dudley (eds.), *Corn and Corn Improvement*, 3rd ed., American Society of Agronomy, Madison, Wis., United States of America, pages 345-387.
Pierik (1999) *In vitro Culture of Higher Plants*, 4th edition. Martinus Nijhoff. Publishers, Dordrecht, The Netherlands.
Risser et al. (1976) *Phytopathology* 66:1105-1106.
Sambrook & Russell (2001). *Molecular Cloning: A Laboratory Manual, Third Edition*, Cold Spring Harbor Laboratory Press, Cold Spring Harbor, N.Y., United States of America.
Sanford (1988). *Trends Biotechnol* 6:299-302.
Sanford (1990) *Physiologica Plantarum,* 79:206-209.
Sanford et al. (1987). *J Particulate Sci Technol* 5:27-37.
Sanford et al., (1993) *Meth Enzymol* 217:483-509.
Stam (1993) *Plant J* 3:739-744.
Tijssen (1993) in *Laboratory Techniques in Biochemistry and Molecular Biology*, Elsevier, New York, N.Y., United States of America.
U.S. Pat. Nos. 4,458,066; 5,591,616.
Utz & Melchinger (1996) *J Agricultural Genomics* 2:1-5.
Van Berloo et al. (2001) *Mol Breeding* 8:187-195.
Zhang et al. (1991) *Biotechnology.* 9:996-997.
Zhao & Stodolsky (2004) *Bacterial Artificial Chromosomes*. Methods in Molecular Biology Vol. 255. Humana Press Inc. Totowa, N.J., United States of America.
Zietkiewicz et al. (1994) *Genomics* 20:176-183.

It will be understood that various details of the presently disclosed subject matter may be changed without departing from the scope of the presently disclosed subject matter. Furthermore, the foregoing description is for the purpose of illustration only, and not for the purpose of limitation.

What is claimed is:

1. A method for the production of an inbred melon plant adapted for conferring, in hybrid combination with a suitable second inbred, resistance to *F. oxysporum* f.sp. *melonis* (FOM) race 1,2, the method comprising:
   (a) selecting a first donor parental line possessing a desired FOM race 1,2 resistance and having a resistant locus mapping to linkage group 9 and mapped by one or more of the markers 9.1, 9.2, and 9.3;
   (b) crossing the first donor parent line with a second parental line in hybrid combination to produce a segregating plant population;
   (c) screening the segregating plant population for identified chromosomal loci of one or more genes associated with the resistance to FOM race 1,2; and
   (d) selecting plants from the population having the identified chromosomal loci for further screening until a line is obtained which is homozygous for resistance to FOM race 1,2 at sufficient loci to give resistance to FOM race 1,2 in hybrid combination.

2. A method for producing melon plants which are resistant to *F. oxysporum* f.sp. *melonis* (FOM) race 1,2 occurring in melon, the method comprising:
   (e) providing a *Cucumis melo* plant which contains one or more alleles that confer resistance to FOM race 1,2, which alleles are present within one or more of five Quantitative Trait Loci QTL1-QTL5 on different chromosomes, wherein:
   (i) QTL1 is defined by the following markers:
      (1) a marker of about 322 basepairs (bp), wherein the marker corresponds to an amplification product generated by amplifying a *Cucumis melo* nucleic acid with a forward primer comprising a nucleotide sequence as set forth in SEQ ID NO: 1 and a reverse primer comprising a nucleotide sequence as set forth in SEQ ID NO: 2; and
      (2) a marker of about 303 bp, wherein the marker corresponds to an amplification product generated by amplifying a *Cucumis melo* nucleic acid with a forward primer comprising a nucleotide sequence as set forth in SEQ ID NO: 3 and a reverse primer comprising a nucleotide sequence as set forth in SEQ ID NO: 4;
      or any part of a DNA sequence as in 03MFR001795 linked within 1, 2, 5, or 10 cM to at least one of the markers of (1) and (2) conferring resistance to FOM race 1,2;
   (ii) QTL2 is defined by the following markers:
      (1) a marker of about 237 bp, wherein the marker corresponds to an amplification product generated by amplifying a *Cucumis melo* nucleic acid with a forward primer comprising a nucleotide sequence as set forth in SEQ ID NO: 5 and a reverse primer comprising a nucleotide sequence as set forth in SEQ ID NO: 6; and
      (2) a marker of about 189 bp, wherein the marker corresponds to an amplification product generated by amplifying a *Cucumis melo* nucleic acid with a forward primer comprising a nucleotide sequence as set forth in SEQ ID NO: 7 and a reverse primer comprising a nucleotide sequence as set forth in SEQ ID NO: 8,
      or any part of a DNA sequence as in 03MFR001795 linked within 1, 2, 5, or 10 cM to at least one of the markers of (1) and (2) conferring resistance to FOM race 1,2;
   (iii) QTL3 is defined by the following markers:
      (1) a marker of about 221 bp, wherein the marker corresponds to an amplification product generated by amplifying a *Cucumis melo* nucleic acid with a forward primer comprising a nucleotide sequence as set forth in SEQ ID NO: 9 and a reverse primer comprising a nucleotide sequence as set forth in SEQ ID NO: 10; and
      (2) a marker of about 229 bp, wherein the marker corresponds to an amplification product generated by amplifying a *Cucumis melo* nucleic acid with a forward primer comprising a nucleotide sequence as set forth in SEQ ID NO: 11 and a reverse primer comprising a nucleotide sequence as set forth in SEQ ID NO: 12,
      or any part of a DNA sequence as in 03MFR001795 linked within 1, 2, 5, or 10 cM to at least one of the markers of (1), and (2) conferring resistance to FOM race 1,2;
   (iv) QTL4 is defined by the following markers:
      (1) a marker of about 329 bp, wherein the marker corresponds to an amplification product generated by amplifying a *Cucumis melo* nucleic acid with a forward primer comprising a nucleotide sequence as set forth in SEQ ID NO: 13 and a reverse primer comprising a nucleotide sequence as set forth in SEQ ID NO: 14;

(2) a marker of about 279 bp, wherein the marker corresponds to an amplification product generated by amplifying a *Cucumis melo* nucleic acid with a forward primer comprising a nucleotide sequence as set forth in SEQ ID NO: 15 and a reverse primer comprising a nucleotide sequence as set forth in SEQ ID NO: 16; and (3) a marker of about 147 bp, wherein the marker corresponds to an amplification product generated by amplifying a *Cucumis melo* nucleic acid with a forward primer comprising a nucleotide sequence as set forth in SEQ ID NO: 17 and a reverse primer comprising a nucleotide sequence as set forth in SEQ ID NO: 18, or any part of a DNA sequence as in 03MFR001795 linked within 1, 2, 5, or 10 cM to at least one of the markers of (1), (2), and (3) conferring resistance to FOM race 1,2; and (v) QTL5 is defined by the following markers:

(1) a marker of about 246 bp, wherein the marker corresponds to an amplification product generated by amplifying a *Cucumis melo* nucleic acid with a forward primer comprising a nucleotide sequence as set forth in SEQ ID NO: 19 and a reverse primer comprising a nucleotide sequence as set forth in SEQ ID NO: 20; and (2) a marker of about 251 bp, wherein the marker corresponds to an amplification product generated by amplifying a *Cucumis melo* nucleic acid with a forward primer comprising a nucleotide sequence as set forth in SEQ ID NO: 21 and a reverse primer comprising a nucleotide sequence as set forth in SEQ ID NO: 22, or any part of a DNA sequence as in 03MFR001795 linked within 1, 2, 5, or 10 cM to at least one of the markers of (1) and (2) conferring resistance to FOM race 1,2; and (f) crossing the *Cucumis melo* plant provided in step (a) with *Cucumis melo* culture breeding material to produce one or more progeny individuals, whereby one or more melon plants which are resistant to *F. oxysporum* f.sp. *melonis* (FOM) race 1,2 occurring in melon are produced.

3. The method of claim 2, further comprising:
(a) collecting the seeds resulting from the cross in step (b);
(b) regenerating the seeds into plants;
(c) evaluating the plants of step (d) for resistance to FOM race 1,2; and
(d) identifying and selecting plants which are resistant to the FOM race 1,2.

4. The method of claim 2, wherein the *Cucumis melo* plant provided in step (a) is 03MFR001795 or an ancestor or descendent thereof.

5. A method for identifying a first *Cucumis melo* plant or germplasm that displays resistance, improved resistance, or reduced susceptibility to FOM race 1,2, the method comprising detecting in the first *Cucumis melo* plant or germplasm at least one allele of one or more marker locus that is associated with the tolerance, improved tolerance, reduced susceptibility, or susceptibility, wherein the one or more marker locus is selected from the group consisting of: (a) 9.1, 9.2, 9.3; (b) a marker locus linked to a marker locus of (a); and (c) a marker locus localizing within a chromosome interval including a marker pair 9.1 and 9.3.

6. The method claim 5, wherein the detecting comprises detecting at least one allelic form of a polymorphic simple sequence repeat (SSR) or a single nucleotide polymorphism (SNP).

7. The method claim 5, wherein the detecting comprises amplifying the marker locus or a portion of the marker locus and detecting the resulting amplified marker amplicon.

8. The method of claim 7, wherein the amplifying comprises employing a polymerase chain reaction (PCR) or ligase chain reaction (LCR) using a nucleic acid isolated from the first melon plant or germplasm as a template in the PCR or LCR.

9. The method claim 5, wherein the at least one allele is a favorable allele that positively correlates with FOM race 1,2 resistance or improved FOM race 1,2 resistance.

* * * * *

SEQUENCE LISTING

```
<160> NUMBER OF SEQ ID NOS: 23

<210> SEQ ID NO 1
<211> LENGTH: 19
<212> TYPE: DNA
<213> ORGANISM: Artificial Sequence
<220> FEATURE:
<223> OTHER INFORMATION: Artificially synthesized oligonucleotide primer
      used to screen for the presence or absence of marker 3.1
<220> FEATURE:
<221> NAME/KEY: misc_feature
<222> LOCATION: (1)..(1)
<223> OTHER INFORMATION: Can optionally include the sequence disclosed
      in SEQ ID NO: 23 placed 5' to nucleotide position 1
```

-continued

```
<400> SEQUENCE: 1
gcgtcatagc gtacttagc                                              19

<210> SEQ ID NO 2
<211> LENGTH: 19
<212> TYPE: DNA
<213> ORGANISM: Artificial Sequence
<220> FEATURE:
<223> OTHER INFORMATION: Artificially synthesized oligonucleotide primer
      used to screen for the presence or absence of marker 3.1

<400> SEQUENCE: 2
atttgttttg ccatttctg                                              19

<210> SEQ ID NO 3
<211> LENGTH: 19
<212> TYPE: DNA
<213> ORGANISM: Artificial Sequence
<220> FEATURE:
<223> OTHER INFORMATION: Artificially synthesized oligonucleotide primer
      used to screen for the presence or absence of marker 3.2
<220> FEATURE:
<221> NAME/KEY: misc_feature
<222> LOCATION: (1)..(1)
<223> OTHER INFORMATION: Can optionally include the sequence disclosed
      in SEQ ID NO: 23 placed 5' to nucleotide position 1

<400> SEQUENCE: 3
ccaaatcgaa acaaaagtc                                              19

<210> SEQ ID NO 4
<211> LENGTH: 19
<212> TYPE: DNA
<213> ORGANISM: Artificial Sequence
<220> FEATURE:
<223> OTHER INFORMATION: Artificially synthesized oligonucleotide primer
      used to screen for the presence or absence of marker 3.2

<400> SEQUENCE: 4
tgttagattt gttgcaggc                                              19

<210> SEQ ID NO 5
<211> LENGTH: 22
<212> TYPE: DNA
<213> ORGANISM: Artificial Sequence
<220> FEATURE:
<223> OTHER INFORMATION: Artificially synthesized oligonucleotide primer
      used to screen for the presence or absence of marker 6.1
<220> FEATURE:
<221> NAME/KEY: misc_feature
<222> LOCATION: (1)..(1)
<223> OTHER INFORMATION: Can optionally include the sequence disclosed
      in SEQ ID NO: 23 placed 5' to nucleotide position 1

<400> SEQUENCE: 5
acaaaatggt aatgaaaact tg                                          22

<210> SEQ ID NO 6
<211> LENGTH: 19
<212> TYPE: DNA
<213> ORGANISM: Artificial Sequence
<220> FEATURE:
<223> OTHER INFORMATION: Artificially synthesized oligonucleotide primer
      used to screen for the presence or absence of marker 6.1

<400> SEQUENCE: 6
aacaagaaag ctaccacgc                                              19
```

```
<210> SEQ ID NO 7
<211> LENGTH: 19
<212> TYPE: DNA
<213> ORGANISM: Artificial Sequence
<220> FEATURE:
<223> OTHER INFORMATION: Artificially synthesized oligonucleotide primer
      used to screen for the presence or absence of marker 6.2
<220> FEATURE:
<221> NAME/KEY: misc_feature
<222> LOCATION: (1)..(1)
<223> OTHER INFORMATION: Can optionally include the sequence disclosed
      in SEQ ID NO: 23 placed 5' to nucleotide position 1

<400> SEQUENCE: 7
cccatgaaag aaaatggag                                                  19

<210> SEQ ID NO 8
<211> LENGTH: 19
<212> TYPE: DNA
<213> ORGANISM: Artificial Sequence
<220> FEATURE:
<223> OTHER INFORMATION: Artificially synthesized oligonucleotide primer
      used to screen for the presence or absence of marker 6.2

<400> SEQUENCE: 8
ttcatcttcc atcaaaccc                                                  19

<210> SEQ ID NO 9
<211> LENGTH: 19
<212> TYPE: DNA
<213> ORGANISM: Artificial Sequence
<220> FEATURE:
<223> OTHER INFORMATION: Artificially synthesized oligonucleotide primer
      used to screen for the presence or absence of marker 7.1
<220> FEATURE:
<221> NAME/KEY: misc_feature
<222> LOCATION: (1)..(1)
<223> OTHER INFORMATION: Can optionally include the sequence disclosed
      in SEQ ID NO: 23 placed 5' to nucleotide position 1

<400> SEQUENCE: 9
tagcttgaac ttcgtcctg                                                  19

<210> SEQ ID NO 10
<211> LENGTH: 19
<212> TYPE: DNA
<213> ORGANISM: Artificial Sequence
<220> FEATURE:
<223> OTHER INFORMATION: Artificially synthesized oligonucleotide primer
      used to screen for the presence or absence of marker 7.1

<400> SEQUENCE: 10
gaagcgtact ccctattgc                                                  19

<210> SEQ ID NO 11
<211> LENGTH: 19
<212> TYPE: DNA
<213> ORGANISM: Artificial Sequence
<220> FEATURE:
<223> OTHER INFORMATION: Artificially synthesized oligonucleotide primer
      used to screen for the presence or absence of marker 7.2
<220> FEATURE:
<221> NAME/KEY: misc_feature
<222> LOCATION: (1)..(1)
<223> OTHER INFORMATION: Can optionally include the sequence disclosed
      in SEQ ID NO: 23 placed 5' to nucleotide position 1

<400> SEQUENCE: 11
ggcagtaaat gaccatgac                                                  19
```

```
<210> SEQ ID NO 12
<211> LENGTH: 19
<212> TYPE: DNA
<213> ORGANISM: Artificial Sequence
<220> FEATURE:
<223> OTHER INFORMATION: Artificially synthesized oligonucleotide primer
      used to screen for the presence or absence of marker 7.2

<400> SEQUENCE: 12
ggtgacgaac aaactgaag                                              19

<210> SEQ ID NO 13
<211> LENGTH: 19
<212> TYPE: DNA
<213> ORGANISM: Artificial Sequence
<220> FEATURE:
<223> OTHER INFORMATION: Artificially synthesized oligonucleotide primer
      used to screen for the presence or absence of marker 9.1
<220> FEATURE:
<221> NAME/KEY: misc_feature
<222> LOCATION: (1)..(1)
<223> OTHER INFORMATION: Can optionally include the sequence disclosed
      in SEQ ID NO: 23 placed 5' to nucleotide position 1

<400> SEQUENCE: 13
tagcaaacga caactaggc                                              19

<210> SEQ ID NO 14
<211> LENGTH: 19
<212> TYPE: DNA
<213> ORGANISM: Artificial Sequence
<220> FEATURE:
<223> OTHER INFORMATION: Artificially synthesized oligonucleotide primer
      used to screen for the presence or absence of marker 9.1

<400> SEQUENCE: 14
gtggaaaaga gaggaaagg                                              19

<210> SEQ ID NO 15
<211> LENGTH: 19
<212> TYPE: DNA
<213> ORGANISM: Artificial Sequence
<220> FEATURE:
<223> OTHER INFORMATION: Artificially synthesized oligonucleotide primer
      used to screen for the presence or absence of marker 9.2
<220> FEATURE:
<221> NAME/KEY: misc_feature
<222> LOCATION: (1)..(1)
<223> OTHER INFORMATION: Can optionally include the sequence disclosed
      in SEQ ID NO: 23 placed 5' to nucleotide position 1

<400> SEQUENCE: 15
cccctcttat cttttcctg                                              19

<210> SEQ ID NO 16
<211> LENGTH: 19
<212> TYPE: DNA
<213> ORGANISM: Artificial Sequence
<220> FEATURE:
<223> OTHER INFORMATION: Artificially synthesized oligonucleotide primer
      used to screen for the presence or absence of marker 9.2

<400> SEQUENCE: 16
catcaagaag tcacggaag                                              19

<210> SEQ ID NO 17
<211> LENGTH: 20
<212> TYPE: DNA
<213> ORGANISM: Artificial Sequence
<220> FEATURE:
```

```
<223> OTHER INFORMATION: Artificially synthesized oligonucleotide primer
      used to screen for the presence or absence of marker 9.3
<220> FEATURE:
<221> NAME/KEY: misc_feature
<222> LOCATION: (1)..(1)
<223> OTHER INFORMATION: Can optionally include the sequence disclosed
      in SEQ ID NO: 23 placed 5' to nucleotide position 1

<400> SEQUENCE: 17
ccaaagtaaa agtgaagtcc                                                    20

<210> SEQ ID NO 18
<211> LENGTH: 20
<212> TYPE: DNA
<213> ORGANISM: Artificial Sequence
<220> FEATURE:
<223> OTHER INFORMATION: Artificially synthesized oligonucleotide primer
      used to screen for the presence or absence of marker 9.3

<400> SEQUENCE: 18
cttgaaatga atttgaggtg                                                    20

<210> SEQ ID NO 19
<211> LENGTH: 18
<212> TYPE: DNA
<213> ORGANISM: Artificial Sequence
<220> FEATURE:
<223> OTHER INFORMATION: Artificially synthesized oligonucleotide primer
      used to screen for the presence or absence of marker 10.1
<220> FEATURE:
<221> NAME/KEY: misc_feature
<222> LOCATION: (1)..(1)
<223> OTHER INFORMATION: Can optionally include the sequence disclosed
      in SEQ ID NO: 23 placed 5' to nucleotide position 1

<400> SEQUENCE: 19
ttctgatcaa cgacgaag                                                      18

<210> SEQ ID NO 20
<211> LENGTH: 19
<212> TYPE: DNA
<213> ORGANISM: Artificial Sequence
<220> FEATURE:
<223> OTHER INFORMATION: Artificially synthesized oligonucleotide primer
      used to screen for the presence or absence of marker 10.1

<400> SEQUENCE: 20
gaaacaaaag cctccattg                                                     19

<210> SEQ ID NO 21
<211> LENGTH: 19
<212> TYPE: DNA
<213> ORGANISM: Artificial Sequence
<220> FEATURE:
<223> OTHER INFORMATION: Artificially synthesized oligonucleotide primer
      used to screen for the presence or absence of marker 10.2
<220> FEATURE:
<221> NAME/KEY: misc_feature
<222> LOCATION: (1)..(1)
<223> OTHER INFORMATION: Can optionally include the sequence disclosed
      in SEQ ID NO: 23 placed 5' to nucleotide position 1

<400> SEQUENCE: 21
acccaccatg cattctaac                                                     19

<210> SEQ ID NO 22
<211> LENGTH: 19
<212> TYPE: DNA
<213> ORGANISM: Artificial Sequence
<220> FEATURE:
```

-continued

```
<223> OTHER INFORMATION: Artificially synthesized oligonucleotide primer
      used to screen for the presence or absence of marker 10.2

<400> SEQUENCE: 22
gagccagttg gggttttag                                              19

<210> SEQ ID NO 23
<211> LENGTH: 17
<212> TYPE: DNA
<213> ORGANISM: Artificial Sequence
<220> FEATURE:
<223> OTHER INFORMATION: Artificially synthesized oligonucleotide primer
      comprising an M13 sequence that can be placed 5' to any of SEQ ID
      NOs: 1, 3, 5, 7, 9, 11, 13, 15, 17, 19, and 21 to detect the size
      of an amplified fragment in a sequencer

<400> SEQUENCE: 23
gttttcccag tcacgac                                                17
```